(12) United States Patent
Sugita et al.

(10) Patent No.: US 7,171,095 B2
(45) Date of Patent: Jan. 30, 2007

(54) OPTICAL DEVICE AND METHOD OF MANUFACTURING THE SAME

(75) Inventors: Mitusuro Sugita, Tokyo (JP); Takao Yonehara, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/545,157

(22) PCT Filed: Aug. 27, 2004

(86) PCT No.: PCT/JP2004/012784

§ 371 (c)(1),
(2), (4) Date: Aug. 11, 2005

(87) PCT Pub. No.: WO2005/022224

PCT Pub. Date: Mar. 10, 2005

(65) Prior Publication Data

US 2006/0147169 A1 Jul. 6, 2006

(30) Foreign Application Priority Data

Aug. 28, 2003 (JP) ............................. 2003-305486
Aug. 25, 2004 (JP) ............................. 2004-244686

(51) Int. Cl.
*G02B 6/10* (2006.01)
*H01L 21/00* (2006.01)
*H01S 3/00* (2006.01)

(52) U.S. Cl. ...................... 385/129; 385/130; 385/131; 385/12; 385/141; 438/29; 438/31; 359/346

(58) Field of Classification Search .................. 385/12, 385/39, 129, 130, 131, 132, 14, 141; 438/29, 438/31; 65/385, 386; 359/346
See application file for complete search history.

(56) References Cited

U.S. PATENT DOCUMENTS 5,682,401 A    10/1997  Joannopoulos et al. ........ 372/96

(Continued)

FOREIGN PATENT DOCUMENTS

DE    100 14 723    9/2001    ............. 385/129 X (Continued)

OTHER PUBLICATIONS

Arrand, et al., "The Application of Porous Silicon to Optical Waveguide Technology," Journal of Selected Topics in Quantum Electronics, vol. 4, No. 6, pp. 975-985 (Nov. 1998).

(Continued)

*Primary Examiner*—Brian M. Healy
(74) *Attorney, Agent, or Firm*—Fitzpatrick, Cella, Harper & Scinto

(57) ABSTRACT

An optical device comprising a substrate, a porous layer laid on the substrate having a pore diameter smaller than the wavelength of light and a crystal layer laid on the porous layer showing a refractive index greater than that of the porous layer is presented. The optical device is manufactured by a method comprising a step of forming a porous layer having a pore diameter smaller than the wavelength of light on the surface of a substrate and a step of forming a crystal layer showing a refractive index greater than that of the porous layer on the porous layer. Since the porous layer is clad, light can be confined with ease.

36 Claims, 20 Drawing Sheets

U.S. PATENT DOCUMENTS

| | | | |
|---|---|---|---|
| 2002/0089620 A1* | 7/2002 | Yamamoto et al. | 349/96 |
| 2003/0036085 A1* | 2/2003 | Salinaro et al. | 435/6 |
| 2003/0203284 A1* | 10/2003 | Iriguchi et al. | 430/1 |
| 2006/0147169 A1* | 7/2006 | Sugita et al. | 385/129 |
| 2006/0193552 A1 | 8/2006 | Sugita | 385/14 |

FOREIGN PATENT DOCUMENTS

| | | | |
|---|---|---|---|
| DE | 101 23 137 | 10/2002 | 385/129 X |
| JP | 2000-144276 | 5/2000 | |
| JP | 2002-299153 | 10/2002 | |

OTHER PUBLICATIONS

St. John et al., "Characterization of Erbium Doped $SiO_2$ Layers Formed on Silicon by Spark Processing," Mat. Res. Soc. Symp. Proc. vol. 486, pp. 281-286 (Dec. 1998).

Arrand, et al., "Solvent Detection Using Porous Silicon Optical Waveguides," Journal of Luminescence, vol. 80, No. 1-4, pp. 119-123 (Dec. 1998).

Uehara, et al., "Porous Silicon Refractive Index Lattices", Phys. Stat. Sol. vol. 182, No. 1, pp. 443-446, (Nov. 2000).

Skryshevsky, "Thin Film PV Module,", Thin Solid Films, Elsevier-Sequoia S.A. Lausanne, CH, vol. 368, No. 1, pp. 125-129 (Jun. 2000).

Topol'ancik, et al., "Fluid Detection With Photonic Crystal-Based Multichannel Waveguides", Appl. Phys. Lett., vol. 82, No. 8, pp. 1143-1145 (Feb. 2003).

Yablonovitch, "Inhibited Spontaneous Emission in Solid-State Physics and Electronics," The American Physical Society, vol. 58, No. 20, pp. 2059-2062 (May 18, 1987).

Wada, K., "Photonic Crystal Technology and its Applications," Silicon Microphotonics, Chapter 19, pp. 252, 257 and 258 CMC Publishing (2002).

Koshiba, M., "Optical Waveguide Analysis," Guided Mode in Optical Waveguide, Chapter 3, pp. 34-35, Asakura-Shoten (1990).

Natomi, M., "Photonic Crystal Slabs Using SOI Slabs," Oyo-Butsuri (Applied Physics), vol. 72, No. 7, pp. 914-918 (2003).

Celler, G. et al., "Status Quo of SOI Wafers for MEMS," Denshi-Zairyo (Electronic Material), pp. 27-31 (May 2002).

\* cited by examiner

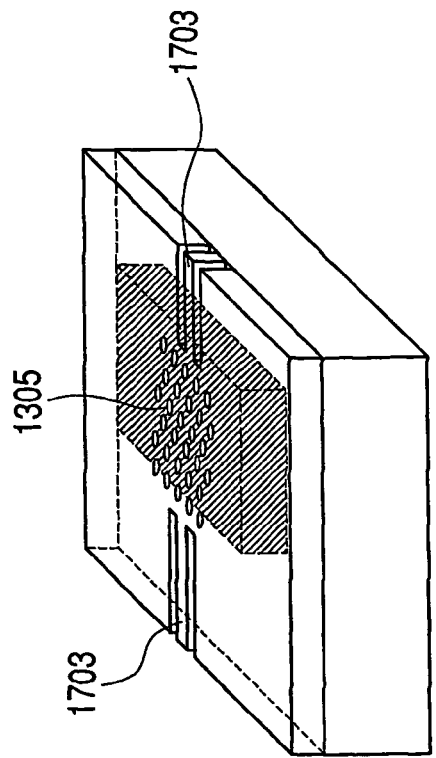
FIG. 17A
FIG. 17C
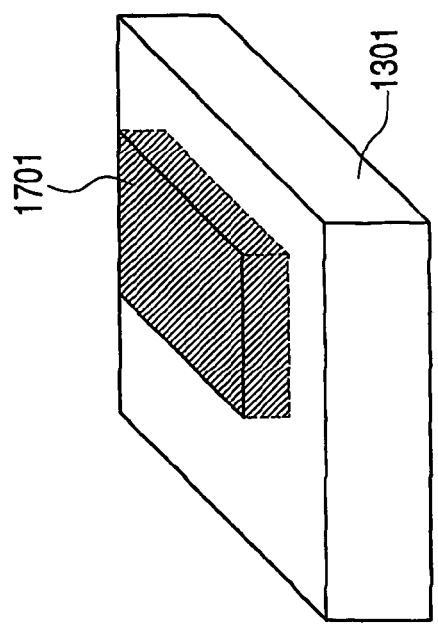
FIG. 17B
FIG. 17D
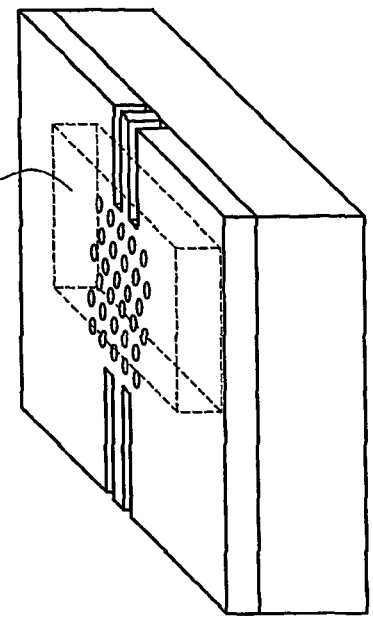
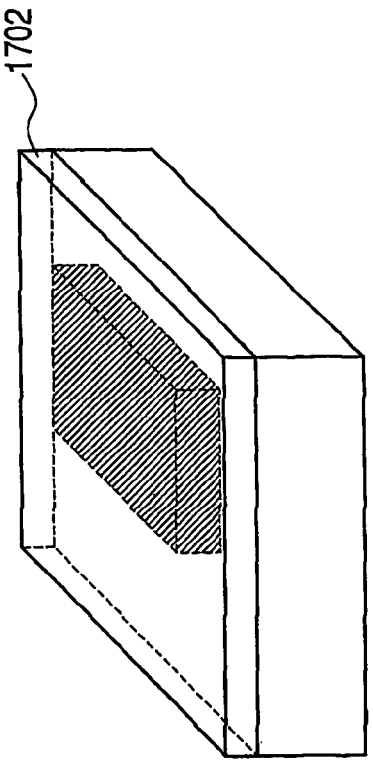

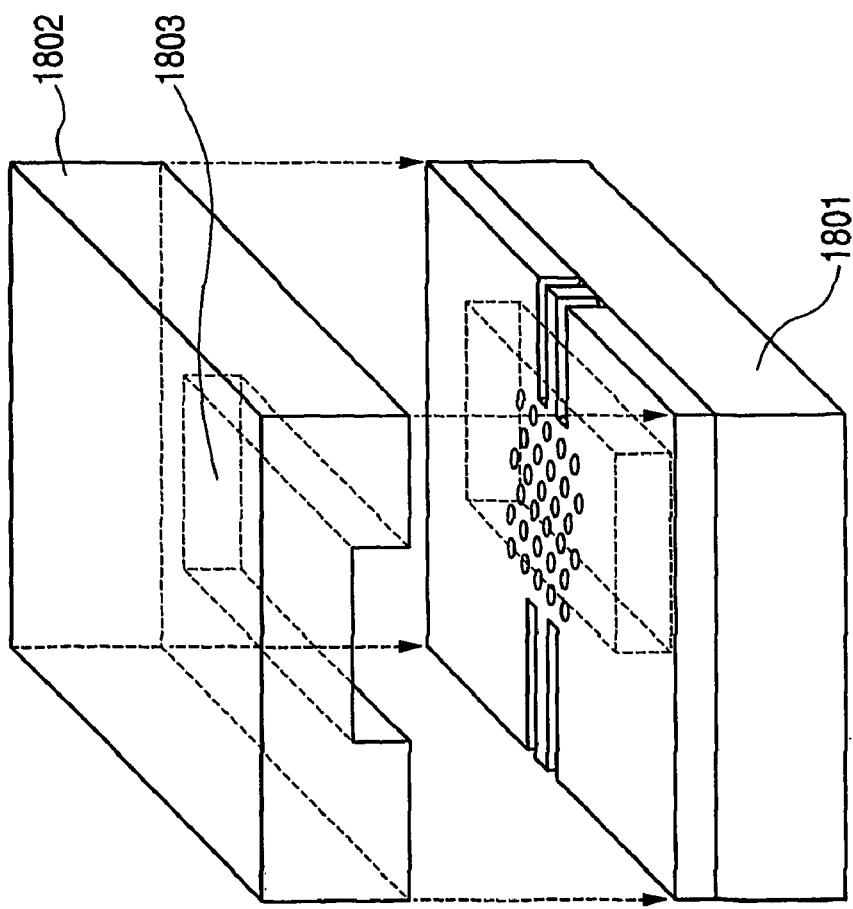
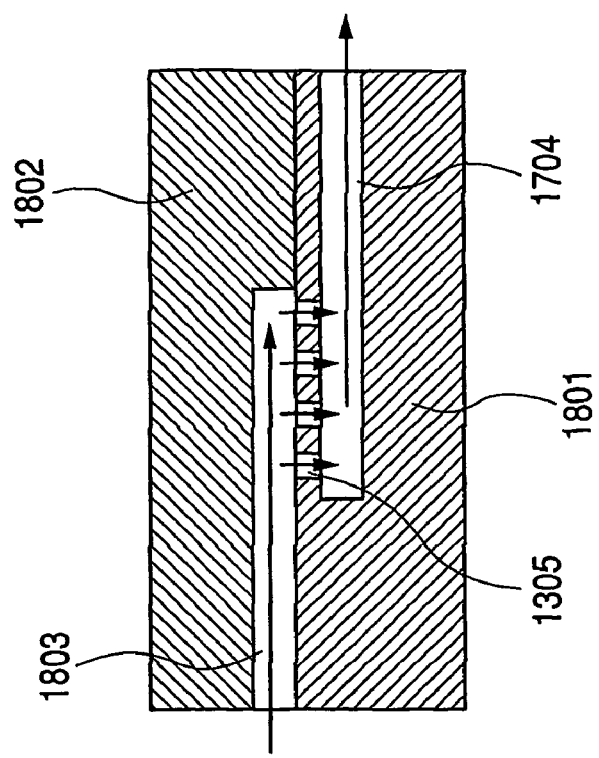
FIG. 18A
FIG. 18B

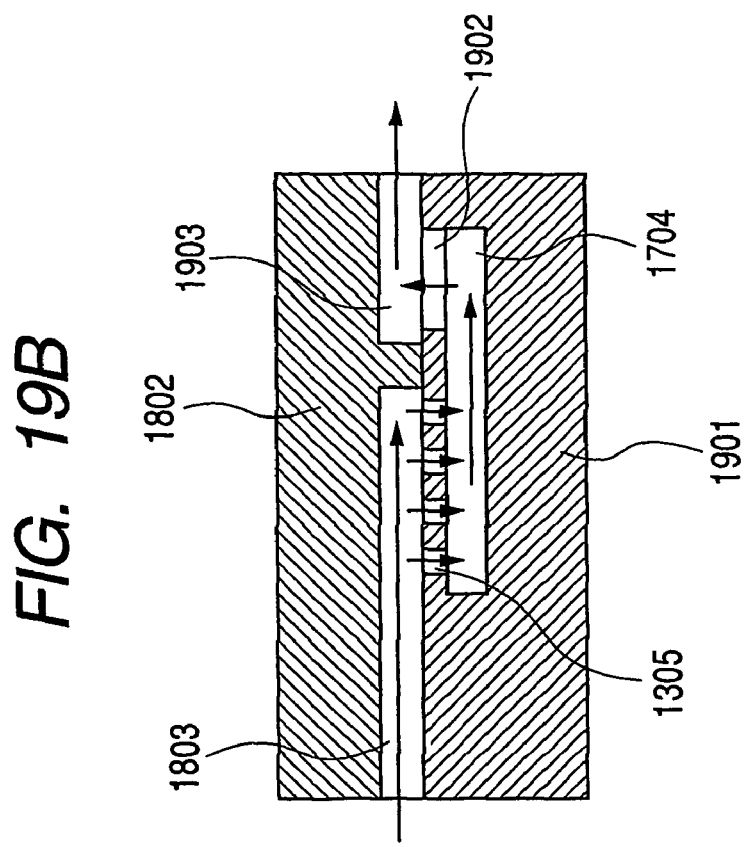
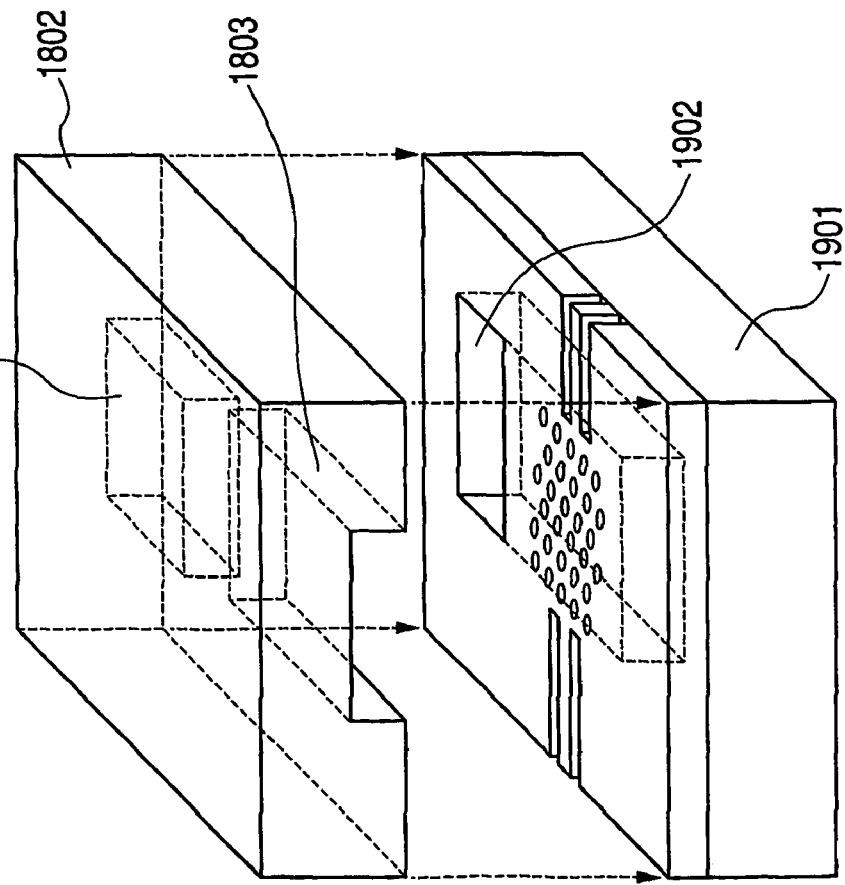
FIG. 19A
FIG. 19B

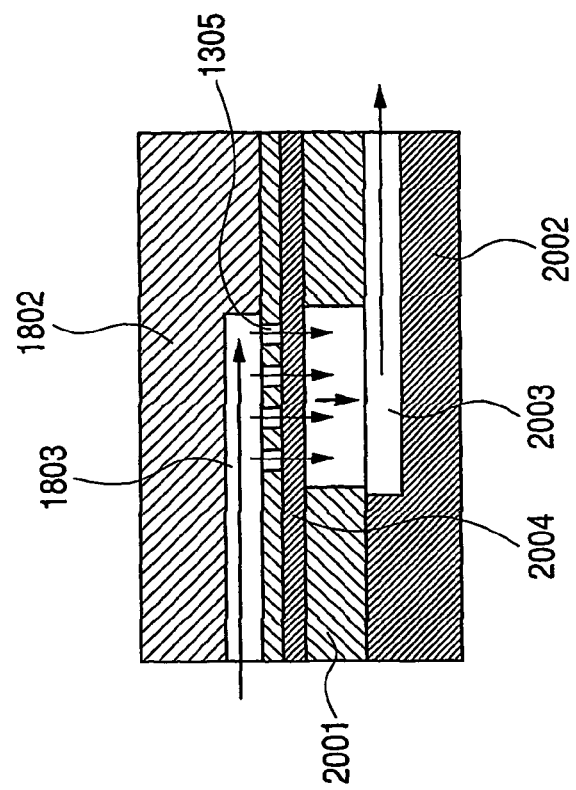
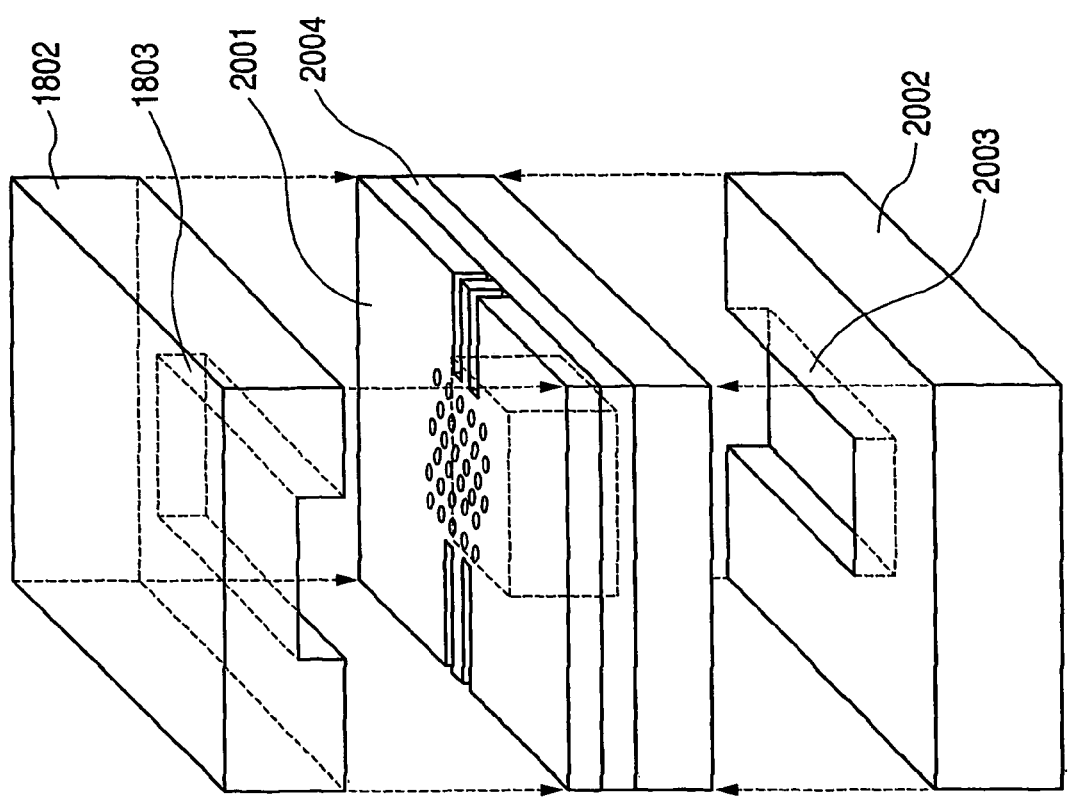
FIG. 20B
FIG. 20A

OPTICAL DEVICE AND METHOD OF MANUFACTURING THE SAME

TECHNICAL FIELD

This invention relates to an optical device and a method of manufacturing the same. More particularly, the present invention relates to an optical device to be used for optical communications and in relation with information processing apparatus that utilize light as well as to a method of manufacturing the same and also to a sensor adapted to highly sensitively detect various pieces of information such as bio information.

BACKGROUND ART

Optical devices of a genre referred to as photonic crystal have been attracting attention in recent years. Yablonovitch: E. Yablonovitch "Phys. Rev. Lett." Vol. 58, p. 2059, 1987 describes that the development of photonic crystals is centered on a technique of producing a periodic distribution of refractive index by forming a periodic structure for an optical material and effectively utilizing the behavior of light in the specific refractive index distribution and a technique of effectively utilizing a phenomenon that light emitting modes can be controlled when a light emitting material is placed in a specific refractive index distribution. The potential of these techniques as applied to optical devices are being discussed.

Relating to the optical device techniques, so-called DFB lasers realized by effectively utilizing a one-dimensional periodic structure for semiconductor lasers have been put to actual use. Such optical devices are produced by applying one-dimensional photonic crystal. At present, efforts are equally being paid for basic research activities in the field of applying two-dimensional photonic crystal having a two-dimensional structure of cylindrical holes that are periodically arranged in a plane to components of optical communication devices. Furthermore, three-dimensional periodic structures referred to as three-dimensional photonic crystals are also known.

Of photonic crystals, two-dimensional photonic crystals are attracting particular attention for several reasons including that they provide a high degree of freedom and hence can be made to operate in a sophisticated way if compared with one-dimensional photonic crystals and that, on the other hand, they can be prepared relatively easily if compared with three-dimensional photonic crystals by utilizing the known semiconductor processing techniques. Basic research activities are in progress for the purpose of developing various devices using two-dimensional photonic crystal. Such devices are highly promising for finding practical applications.

Devices of different types using two-dimensional photonic crystal are objects of current researches. They include micro-waveguide circuits, wavelength filters and micro-lasers to be used as optical communication devices. Kawakami et al., "Photonic Crystal Technology and its Applications" (CMC Publishing, 2002), pp. 252, 257 and 258 describes such devices.

As for the field of the biotechnology and the related industry that has been growing remarkably in recent years, the applicant of the present patent application has proposed "a Micro-Sensor Using a Micro-Resonator Laser" in Japanese Patent Application No. 2002-299153 as an application of two-dimensional photonic crystal to a highly integrated and highly sensitive biosensor chip.

Of two-dimensional photonic crystals that are objects of researches for the purpose of actually developing devices, two-dimensional slab type photonic crystals have been prepared most numerously. The slab type refers to the one in which light is confined in a direction not showing any periodic structure by sandwiching a high refractive index core layer between low refractive index clad layers so that light is confined to the high refractive index core layer for propagation.

The thickness of the slab, or the core layer, is related to the conditions on which an electromagnetic wave mode of light can exist in the direction of the thickness. Particularly, in a case where only a single mode can exist, the optical path length obtained by multiplying the slab thickness by the refractive index is approximately about a half of the wavelength. Thus, the optical path length of a single round trip is approximately equal to the wavelength. In other words, this provides the smallest thickness for allowing light that makes a single round trip to interfere with light that makes several round trips so as to raise the intensity of light. In reality, the thickness is computed by taking the propagation of light to the clad layer into consideration (see Koshiba, "Optical Waveguide Analysis", 1990, Asakura-Shoten)

SOI wafers formed by using an $SiO_2$ layer (BOX (buried oxide) layer) that is formed on an Si substrate as clad and forming an Si layer (SOI (silicon on insulator) layer) thereon as core have been attracting attention in recent years as two-dimensional slab type photonic crystals (see Notomi, "Applied Physics", Vol. 72, No. 7, 2003, "Photonic Crystal Slabs Using SOI Slabs").

The use of such an Si type material provides advantages including (1) the currently available SOI wafer preparing techniques are already feasible so that the necessary precision level can be attained and (2) the currently available sophisticated Si process techniques can be applied to forming a periodic pattern on an SOI layer to be used for a core layer.

Other areas of utilization of SOI wafers for two-dimensional (2D) slab type optical devices include Si fine wire waveguides. As in the case of two-dimensional slab type photonic crystals, researches and developments are under way for confining light to micro-waveguides of 1 μm or less and realizing curved waveguide devices with a small radius of curvature by utilizing a large refractive index difference between Si and $SiO_2$ (see, above-cited Kawakami's paper, p. 252).

However, when such an SOI wafer is used for a 2D slab type photonic crystal or a fine wire waveguide, it is necessary to use relatively thick BOX layers typically having a thickness of 1 μm or more because of the requirements to be met for confining light. When light is confined to a core layer, it can propagate into the clad layer as pointed out above and, if the clad layer is thin, propagating light of the evanescent mode is coupled with light of the radiation mode directed to the substrate to give rise to a radiation loss in a direction toward the substrate. The above cited Kawakami's paper, pp. 257 and 258, describes a calculated thickness necessary for the BOX layer when the allowable loss is −40 dB.

To prepare an SOI wafer comprising BOX layers having a thickness of 1 μm or more, a so-called bonding technique needs to be used. Such techniques are described in Celler and Yasuda, "Status Quo of SOI Wafers for MEMS", 2002. 5, Electronic Technology and also in Iyer and Auberton-Herve, "SILICON WAFER BONDING TECHNOLOGY for VLSI and MEMS applications" (EMIS PROCESSING—SERIES 1, ISBN 0 85296 0395, 2002, The Institution of Electrical Engineers.

However, a process of bonding wafers inevitably includes a bonding step along with a seed wafer cutting step and a plurality of starting wafer preparation steps including special steps such as an H+ ion implanting step and other complex steps. Consequently, the structure of the device to be prepared on such a wafer and the device preparation process are very special if compared with ordinary Si wafers. Then, the prepared SOI wafer is very expensive so that the applications of such wafers are limited only to semiconductor logic circuits such as CPUs having a high added value that makes the use of such wafers economically feasible.

This invention is intended to dissolve the above identified problems of the background art and it is an object of the present invention to provide a highly functional high precision optical device realized by using two-dimensional slab type photonic crystal or a fine wire waveguide having a porous layer as clad.

Another object of the present invention is to provide a method of manufacturing a highly functional high precision optical device having a large area and realized by using two-dimensional slab type photonic crystal or a fine wire waveguide at low cost.

DISCLOSURE OF THE INVENTION

In an aspect of the present invention, there is provided an optical device comprising a substrate, a porous layer laid on the substrate having a pore diameter smaller than the wavelength of light and a crystal layer laid on the porous layer showing a refractive index greater than that of the porous layer. Preferably, an optical device according to the invention is adapted to operate as an optical resonator, a laser resonator in particular.

In another aspect of the invention, there is provided a method of manufacturing an optical device characterized by comprising a step of forming a porous layer having a pore diameter smaller than the wavelength of light on the surface of a substrate and a step of forming a crystal layer showing a refractive index greater than that of the porous layer on the porous layer.

In still another aspect of the invention, there is provided a sensor comprising a porous layer having a pore diameter smaller than the wavelength of light, a crystal layer showing a refractive index greater than that of the porous layer and laid on the porous layer, a region in the crystal layer showing a periodic distribution of refractive index, a flow channel for flowing fluid in the vicinity of the region and a means for irradiating light onto the region and detecting light emitted from the region.

BRIEF DESCRIPTION OF THE DRAWINGS

FIGS. 17A, 17B, 17C and 17D are schematic views of a photonic crystal device of Example 10, showing the configuration thereof and a method of preparing the same;

FIGS. 18A and 18B are schematic views of a flow-through type photonic crystal sensor of Example 10, showing the configuration thereof and a method of preparing the same;

FIGS. 19A and 19B are schematic views of a flow-through type photonic crystal sensor of Example 10, showing an alternative configuration thereof and a method of preparing the same;

FIGS. 20A and 20B are schematic views of a flow-through type photonic crystal sensor of Example 10, showing another alternative configuration thereof and a method of preparing the same;

FIGS. 22A, 22B, 29C and 22D are schematic views of an alternative device of Example 12, showing the configuration thereof.

BEST MODE FOR CARRYING OUT THE INVENTION

An optical device according to the invention is a highly functional high precision optical device realized by using two-dimensional slab type photonic crystal or a fine wire waveguide having a porous layer as clad and can find applications in optical communications, information processing apparatus adapted to use light and various highly sensitive sensors for detecting various pieces of information such as bio information.

While the present invention is described below by way of examples, the present invention is by no means limited to the embodiments described in those examples, which may be modified and altered without departing from the scope of the invention in terms of sequence of operation and other aspects.

While the present invention is described below in terms of materials including Si, GaAs, Ge and GaP, the present invention is by no means limited thereto and compound semiconductors of the III–V type such as AlGaAs, InGaAs, InAs, GaInNAs, InGaP and InP and those of the II–VI type such as CdSe and Cds as well as combinations of epi-grown (epitaxially grown) materials and seed substrate materials showing lattice constants and linear expansion coefficients that are close to each other can also be used for the purpose of the invention.

EXAMPLE 1

This example provides a 2D slab type photonic crystal device realized by using a porous Si layer and an epi-Si layer respectively as clad and core on an Si substrate. Now, a photonic crystal device of this example will be described by referring to FIGS. 1A through 1C.

Figure 1A:
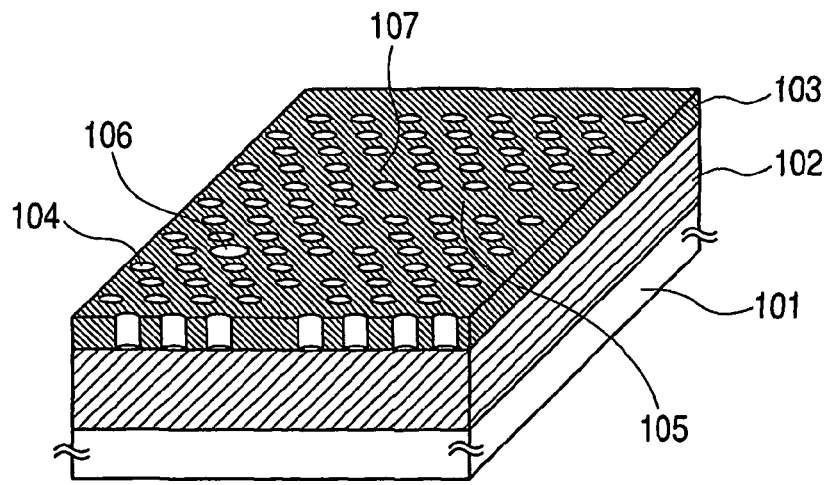
FIGS. 1A, 1B and 1C are schematic views of a 2D slab type photonic crystal device using porous Si for the clad layer of Example 1.
Figure 1B:
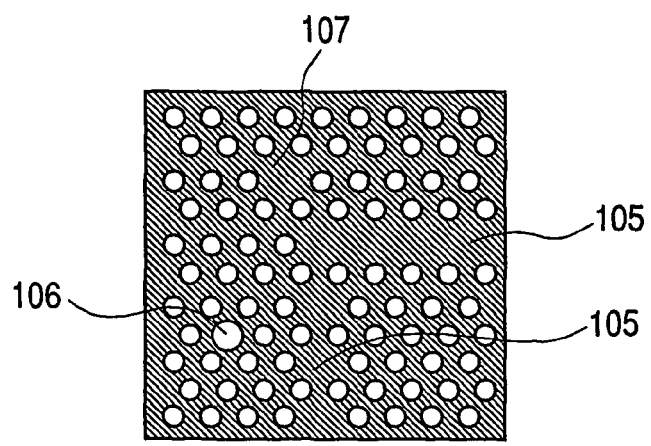
Figure 1C:
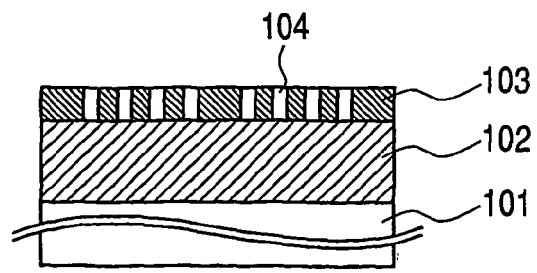

Referring to FIGS. 1A through 1C, a porous Si layer 102 is formed on an Si substrate 101 to a thickness of about 1 μm and then a single crystal Si layer (epi-grown Si layer) 103 is formed thereon by epitaxial growth to a thickness of about 0.2 μm. A pattern 104 of cylindrical holes is formed in the single crystal Si layer 103 to show a triangle lattice. The cylindrical holes are formed to run through the single crystal layer. The cylindrical holes have a diameter and a cycle of arrangement that are substantially equal to the wavelength of light so that only a part that shows a specific wavelength of the light being propagated in an intra-planar direction through the region of the single crystal layer 103 where the pattern is formed is reflected or made to turn its moving direction in a well-known manner.

A 2D slab type photonic crystal device according to the present invention is characterized in that the single crystal layer is held in contact with air along the top surface thereof and with the porous layer 102 along the bottom surface thereof and, since the single crystal layer shows a refractive index that is greater than the refractive index of air and that of the porous layer 102, light is subjected to intra-planar confinement. In other words, the single crystal layer operates as core layer relative to the light being propagated and the porous layer operates as clad layer. Thus, it is possible to prepare a waveguide that gives rise to little loss of light or a resonance structure that shows a high Q value by using a 2D slab type photonic crystal device according to the invention.

The porous Si layer 102 is formed in such a way that the pore diameter of its pores is sufficiently smaller than the wavelength of light, e.g., as small as 1/100 of the wavelength of light to be used with it. Since the pore diameter is sufficiently smaller than the wavelength of light, light is neither scattered nor deflected by any of the pores of the porous layer and hence only shows an average refractive index of light. The 2D slab type photonic crystal device of this example is adapted to an optical wavelength of 1.5 μm and the pore diameter is about 2 nm. The device is prepared in such a way that the porosity of the device is about 80% and the volumetric ratio of Si and air is about 2:8.

The average refractive index (to be referred to as effective refractive index hereinafter) of the porous Si layer can be approximately determined by using formula (1) below and is about 1.5;

$$n_{eff} = n_{air} \times x_{air} + n_{si} \times x_{si} \quad (1),$$

where $n_{eff}$ is the effective refractive index, $n_{air}$ is the refractive index of the air filling the void pores, $X_{air}$ is the porosity, $n_{si}$ is the refractive index of Si and $x_{si}$ is the volumetric ratio of Si, which is equal to $1-x_{air}$. Since the refractive index $n_{si}$ of silicon is 3.5, $$n_{eff} = 1.0 \times 0.8 + 3.5 \times 0.2 = 1.5.$$

This value is substantially equal to the corresponding value of the $SiO_2$ in the BOX layer of conventional SOI wafers. Since the difference Δn between it and the refractive index, or about 3.5, of the epi-Si layer, which is the core layer, is about 2, it is possible to strongly confine light. The fact that it is possible to strongly confine light means that light can be made to locally exist within a small volume when the device is used as an optical waveguide or a resonator and hence it is possible to realize a micro-optical device with an enhanced degree of integration.

The pattern 104 of periodic arrangement of airholes formed through the crystal layer may show a square lattice, a honeycomb lattice or some other lattice pattern instead of the above described triangle lattice.

The periodic pattern 104 may include line defects 105 or point defects 106 that are in fact not pores or point defects 107 whose diameters differ as a function of location in the crystal layer.

Of such defects, line defects can operate as optical waveguide that confines and propagates light along the lines while point defects can operate as optical resonator that makes light exist locally in and/or near them and confines it there. Thus, such defects can be designed and arranged freely depending on the application of the device. An optical resonator can be formed by combining line defects and point defects in any of possible various different ways depending on the space mode of light, introduction of light from and emission of light to the waveguide and other factors.

In the following description, the expression of periodic structure may or may not include linear and/or point defects.

Thus, a 2D slab type photonic crystal device using a porous Si clad layer that has a configuration as described above optically performs very well and provides features that make the device adapted to a high degree of integration like a 2D slab type photonic crystal device using SOI particularly from the viewpoint of the above described effective refractive index. At the same time, it provides additional advantages including that it can be realized at low cost by using a single material to simplify the manufacturing process.

While the effective refractive index of the clad layer is 1.5 and the difference of refractive index between it and the approximately 0.2 μm thick core layer is about 2 in this example, a smaller refractive index may be used for the purpose of the invention. If a smaller refractive index is used, the core layer is made to have a thickness greater than 0.2 μm. Then, it is possible to reduce the porosity of the clad layer.

EXAMPLE 2

This example shows a method of preparing a 2D slab type photonic crystal device described in Example 1.

The method of preparing a photonic crystal device of this example will be described below by referring to FIGS. 2A through 2D.

Figure 2A:
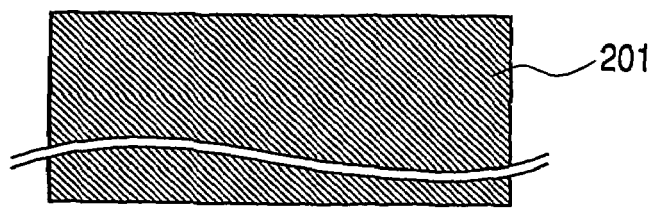
FIGS. 2A, 2B, 2C and 2D are schematic views of a 2D slab type photonic crystal device using porous Si for the clad layer of Example 2.
Figure 2B:
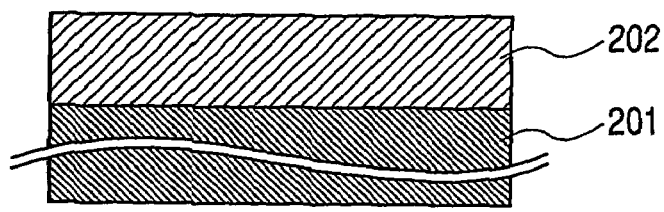

Firstly, a silicon layer 202 having a porous structure is formed on an Si substrate 201 as shown in FIG. 2A by anodization on the surface (FIG. 2B).

It is well known that, when an electrochemical reaction is caused by using an Si substrate as anode and flowing an electric current in a hydrofluoric acid solution, the pits (etch pits) formed on the surface are extended to give rise to void pores. As the void pores continue to grow at the front ends thereof, a porous layer is formed in the surface of the Si substrate to show a structure in which fine and oblong pores extend from the surface. The porous layer of a 2D slab type photonic crystal device according to the invention is formed by utilizing this phenomenon. The porous layer maintains the crystal bearing of the original Si single crystal substrate and, as will be described in greater detail hereinafter, it is possible to epitaxially grow the single crystal thereon.

Figure 3:
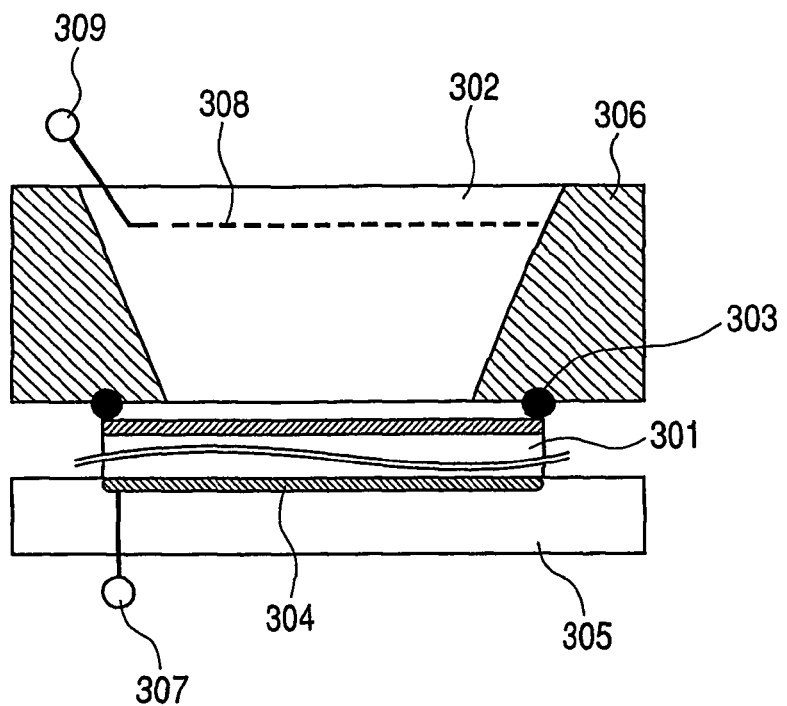
FIG. 3 is a schematic illustration of a method of producing pores by anodization of Example 2.

Conditions for Anodization:
starting wafer: $p^+$Si (100) 0.01 Ωcm
solution: a mixed solution of HF, $C_2H_5OH$ and $H_2O$
anodization current: 150 mA/cm$^2$ The anodization can be conducted by using an apparatus as shown in FIG. 3. Referring to FIG. 3, an Si wafer (substrate) 301 is held in such a way that its epi-Si layer is immersed in HF solution 302. The Si wafer is held in position by a loser support body 305 and an upper support body 306 by way of an O-ring 303 and a Pt-made surface electrode 304. An HF containing liquid tank is arranged in the upper support body 306 so as to communicate with the Si wafer 301 and is filled with HF solution 302. A Pt-made mesh electrode 308 is arranged in the HF solution 302. The Pt-made surface electrode 304 and the Pt-made mesh electrode 308 are connected respectively to anode 307 and cathode 309 so that carriers are injected when a predetermined electric field is applied to the Si by way of the HF solution 302 at the anode side and by way of the rear surface of the Si substrate at the anode side. However, it should be noted that the arrangement for anodization is not limited to the one described in this example and any of various known appropriate arrangements may alternatively be used for the purpose of the invention.

Figure 4:
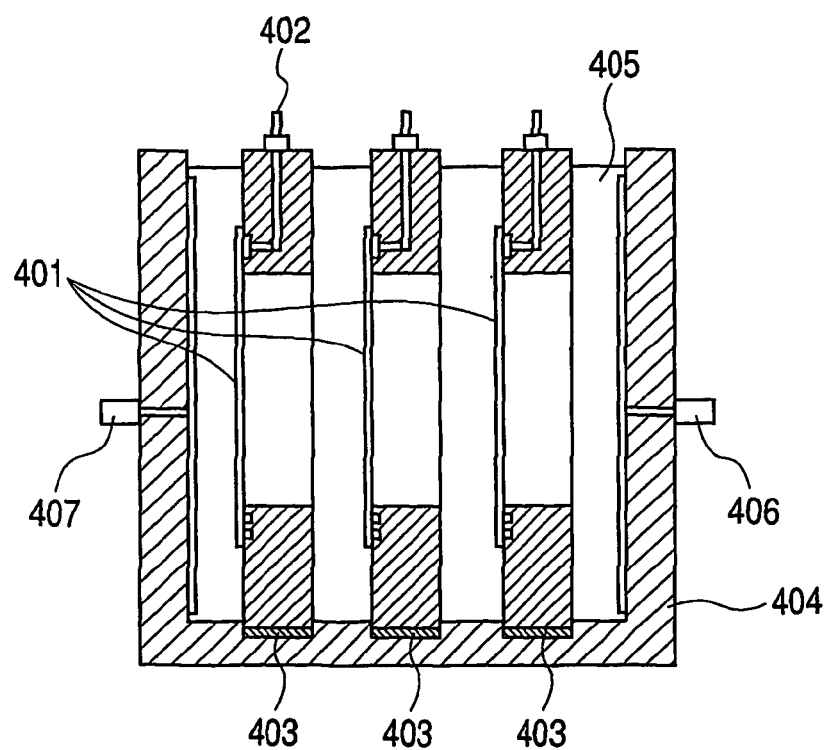
FIG. 4 is a schematic illustration of another method of producing pores by anodization of Example 2.

A plurality of wafers can be collectively processed on a batch basis by means of the apparatus of FIG. 4. The process of anodization becomes less expensive when wafers are treated on a batch basis.

The pore diameter, the density and the thickness of the porous silicon layer can be controlled over a wide range by way of the composition of the solution for the anodization, the anodization current and the conductivity type and the electric conductivity of the substrate. Platinum or a metal coated with platinum is used for the electrodes because platinum can strongly withstand hydrofluoric acid. When a plurality of wafers are collectively subjected to anodization to form porous layers, the anodization solution that contacts the opposite surfaces of the wafers operates as electrode as shown in FIG. 4. Then, the electrode can uniformly contact the wafers to enhance the controllability of the process of forming the porous layers. The porous layer that is formed in this way maintains the crystal bearing of the original single crystal substrate so that it is possible to epitaxially grow a uniform single crystal layer on top.

Figure 2C:
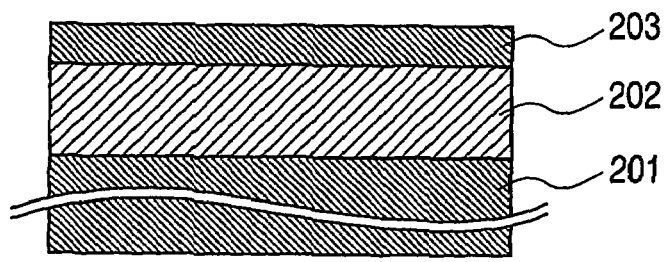

Then, an epi-Si layer 203 is formed on the porous Si layer 202 by epitaxial growth, typically using a chemical vapor deposition (CVD) method (FIG. 2C). It is important for this operation to be conducted in a hydrogen atmosphere because such an atmosphere seals the pores on the surface of the porous layer in an accelerated manner and it is possible to form a high-quality epitaxial layer on top (Yonehara et al., Oyo-Buturi (Applied Physics) 2002 Comprehensive Reports, September Issue).

Figure 2D:
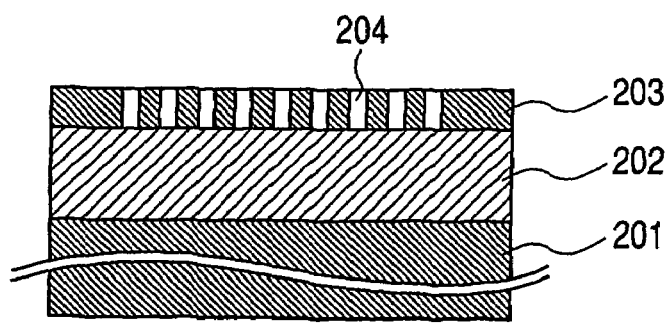

Conditions for Epitaxial Growth:
vapor phase growth temperature; 1,000° C.
gas: $SiH_4/H_2$
pressure: 700 Torr Then, resist is applied onto the epi-Si layer 203 and a periodic pattern 204 is formed by photolithography to form a mask. The single crystal epitaxial silicon layer is removed by etching by way of the mask to form cylindrical holes (FIG. 2D). At this time, the lower porous layer is left to remain there so as to operate as clad layer. The silicon layer is etched on the following conditions.

Etching Conditions:
reactive ion etching
gas: $Cl_2$ type gas

Note that the silicon layer may be etched alternatively by using Br based gas or by means of ECR plasma etching, ICP plasma etching or wet etching, if appropriate. It may be needless to say that resist may be replaced by $SiO_2$ or some other appropriate substance for the mask of the etching operation.

When producing cylindrical holes in the epitaxial silicon single crystal layer grown on the porous silicon layer, it is desirable to use a selective etching technique that automatically stops the etching operation when the porous silicon layer becomes exposed.

It is known that porous silicon is generally highly reactive if compared with non-porous silicon because the surface area of porous silicon is very large relative to the volume thereof (about hundreds of several square meters per cubic centimeter). Remarkable examples of application of porous silicon include enhanced etching, enhanced oxidation and drug delivery using the harmless bio solubility thereof.

Therefore, the porous silicon layer can hardly operate to stop the operation of etching the epitaxial silicon layer. However, it can be used for that purpose by uniformly covering the lateral walls of the pores of the porous silicon with thin oxide film. This will be described below.

Due to the mechanism of anodization of pores, all the pores are formed as the front ends thereof are extended. Therefore, the pores on the surface communicate with the respective front ends before the epitaxial growth. Thus, as a result of thermal oxidation, oxygen is supplied to the fine front ends to form a uniform oxide film coat. Note that the thermal oxidation needs to be conducted at a low temperature lower than 500° C. At this temperature level, the volumetric ratio of the void pores, or the porosity, does not change as a result of oxidation. If, however, the lateral walls of the void pores are subjected to thermal oxidation at a temperature higher than the above cited temperature level, silicon atoms can move on the surfaces of the pores to deform and sometimes close the pores.

As an epitaxial layer is made to grow on the porous film in which the lateral walls of the void pores are oxidized, the porous layer can be used as etching stop layer when etching the epitaxial layer. Selective etching between silicon and silicon oxide is known in reactive ion etching (RIE). The epitaxial layer and the porous layer in which the lateral walls of the pores carry an oxide film coat can be selectively etched by modifying the conditions of the above selective etching. The selectivity rises and, at the same time, the refractive index of the porous layer falls as thickness of the oxide film coat is increased.

As the pore surfaces of the porous layer is coated with oxide silicon film in a manner as described above, it is now possible to stop the etching at the porous layer when forming cylindrical holes in the epitaxial silicon layer so that a two-dimensional photonic crystal slab can be prepared accurately at low cost in order to effectively confine light. Then, it is possible to form various optical circuits.

Figure 23A:
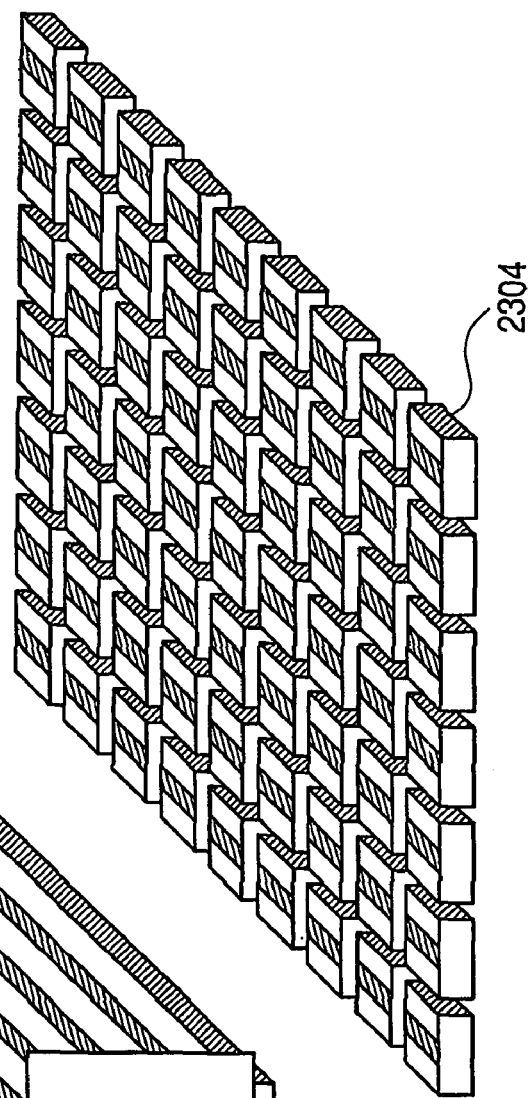
FIGS. 23A and 23B are schematic views of a method of preparing the device of Example 2.
Figure 23B:
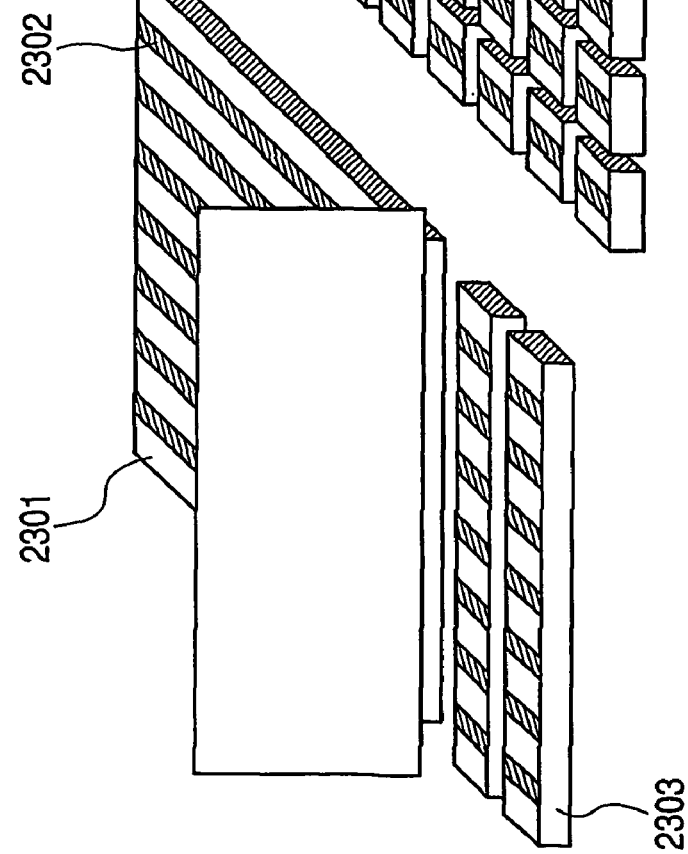

For forming a chip of optical circuit devices and mounting it on any of various systems, a cleaving/dicing technique for separating the devices from the wafer as shown in FIGS. 23A and 23B can be used. With this technique, a partial wafer 2301 obtained by dicing a large wafer is firstly cleaved in a direction substantially perpendicular to the optical waveguide direction of the optical waveguide device pattern 2302 to divide the partial wafer into a plurality of bar wafers 2303 (FIG. 23A). Subsequently, the bar wafers 2303 are diced in a direction perpendicular to the longitudinal direction thereof to divide them into individual devices 2304 (FIG. 23B). The bar wafer is cleaved because signal input/output operations of each of the optical circuit devices are conducted by way of end facets thereof and the smoother the end facets, the higher the input/output efficiency, or the optical coupling efficiency, to improve the performance of the system. With a method according to the invention, the core layer for optical waveguide, the clad layer and the substrate are all made to show a single crystal structure so that flat end facts can easily be produced by cleavage if the intra-planar direction of the patterning operation is aligned with the crystal bearing. Thus, a method according to the invention provides a remarkable advantage particularly from the viewpoint of mass production if compared with a method of using a bonded SOI layer because the crystal bearing of the substrate differs from that of the SOI layer.

In this example, a cylindrical hole pattern showing a triangle lattice and including a defect waveguide or defect resonator similar to that of Example 1 is formed as periodic pattern 204. The diameter of cylindrical holes is about 0.3 μm, which is equal to about ¼ of the operating optical communication band of 1.5 μm, and the pattern cycle is about 0.7 μm.

Meanwhile, beside photolithography described above as patterning technique of this example, nano-imprinting that is less expensive, X-ray lithography that provides a higher resolution, ion beam lithography, EB lithography or optical near field lithography may selectively be used depending on the application of the device.

When oxidizing the porous layer, the porous layer may be subjected to an oxidation process once again after such a patterning operation, where oxygen is introduced through a plurality of cylindrical holes and the oxidation process is continued by using the selectivity thereof until all the porous Si becomes $SiO_2$ so that the produced porous $SiO_2$ may be used for the clad layer.

Thus, a 2D slab type photonic crystal device that does not require any bonding operation is prepared with the method of this example.

EXAMPLE 3

In this example, a method of preparing a 2D slab type photonic crystal device as described above in Example 1 that is different from that of Example 2 is used. The method of this example differs from that of Example 2 in that a crystal Si layer is formed on a porous layer not by epitaxial growth but by annealing a porous Si layer.

Now, the method of preparing a photonic crystal device of this example will be described below by referring to FIGS. 13A through 13G.

Figure 13A:
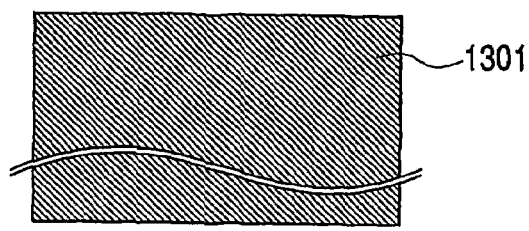
FIGS. 13A, 13B, 13C, 13D, 13E, 13F and 13G are schematic views of a photonic crystal of Example 3, showing the configuration thereof and a method of preparing the same.
Figure 13E:
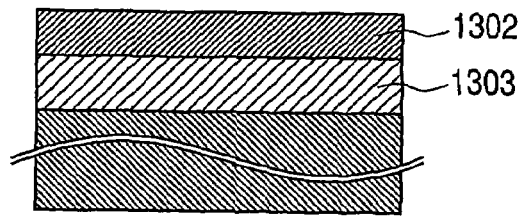
Figure 13B:
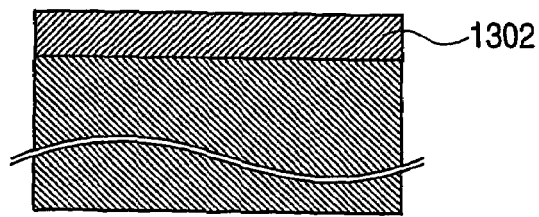
Figure 13F:
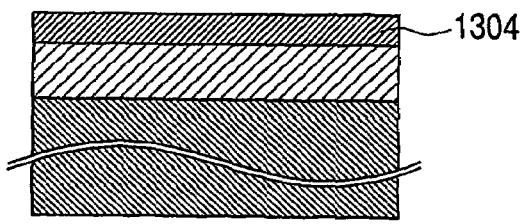
Figure 13C:
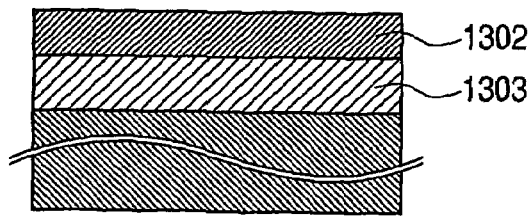

Firstly, an Si substrate 1301 illustrated in FIG. 13A is prepared and two porous silicon layers 1302 and 1303 are formed by means of a two-stage anodization technique on the Si substrate 1301 as shown in FIGS. 13B and 13C. The two porous silicon layers show respective porosities that are different from each other. More specifically, the porosity of the upper porous Si layer 1302 is made to be lower than that porosity of the lower porous Si layer 1303.

As in Example 2, a device showing a configuration as shown in FIG. 3 is used for the anodization.

The porosity of each of the porous layers is controlled by the anodization current used. In this example, the upper porous layer 1302 that shows a small porosity is formed firstly by using a relatively small electric current in the step of FIG. 13B and then the electric current is raised to form the lower porous layer 1303 that shows pores with a large pore diameter in the step of FIG. 13C.

Conditions for Anodization:
  starting wafer: $p^+Si$ (100) 0.01 Ωcm
  solution: HF, $C_2H_5OH$ and $H_2O$
  anodization current: 30 mA/cm$^2$ (upper layer), 150 mA/cm$^2$ (lower layer)

Figure 13G:
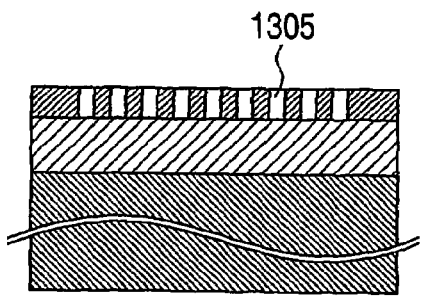
Figure 13D:
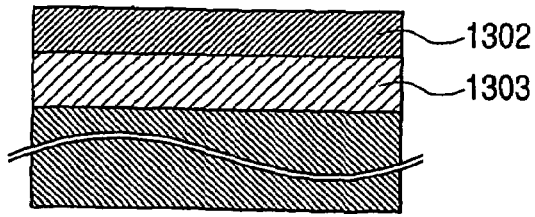

Then, the lateral walls of the pores of the porous silicon are uniformly and very thinly coated with oxide film (FIG. 13D). Due to the mechanism of anodization of pores, all the pores are formed by extention of the front ends thereof. Therefore, the pores at the surface continuously communicate with the respective front ends. Thus, oxygen is supplied to the fine front ends to form, as a result of thermal oxidation, a uniform oxide film coat to both of upper and lower porus layers as schematically illustrated in FIG. 13D. Note that the thermal oxidation needs to be conducted at a low temperature lower than 500° C. so as not to reduce the porosity.

Conditions for Oxidation:
  gas: $O_2$
  temperature: 400° C.

Then, only the oxide film coat formed on the upper porous Si layer 1302 is removed by an HF solution (FIG. 13E).

Thereafter, a hydrogen annealing operation is conducted on the conditions listed below.

Annealing Conditions:
  gas: 100% $H_2$
  temperature: 1,050° C.

Hydrogen annealing is a heating process that is conducted in a hydrogen atmosphere. As a result of hydrogen annealing, Si atoms in the upper porous Si layer 1302 not covered by the oxide film coat and its vicinity moves to fill the void pores and form a continuous crystal layer 1304 as shown in FIG. 13F. At the same time, the surface is smoothed to an atomic level to produce a high quality optical waveguide core structure where, particularly, unwanted scattering of light by the surface roughness of the order of 1/10 of the wavelength of light is suppressed. Since the lower porous layer is not covered by an oxide film coat, void pores are maintained there. Then, there is produced a light confining structure where the crystal layer 1304 formed by the annealing operates as optical waveguide and the lower porous layer 1302 showing a low effective refractive index operates as clad.

As described above, a crystal layer is formed not by using epitaxial growth but by using hydrogen annealing in this example. Thus, the process is simple and does not use $SiH_4$ and other similar gas.

Thereafter, as shown in FIG. 13G, a periodic pattern of cylindrical holes 1305 is formed on the crystal Si layer 1304 by removing the silicon layer by etching, using a photolithography technique as in Example 2. The lower porous layer is left to remain there so as to operate as clad layer. The silicon layer is removed by reactive ion etching using $SF_6+CHF_3$ gas.

It is possible to execute further oxidization process following the step of FIG. 13G. In this process, an oxigen gas is introduced through the cylindrical holes 1305 to oxidize the lower porus Si layer 1303 almost wholely to $SiO_2$, which is preferable as a clad layer.

EXAMPLE 4

In this example, another method of preparing a 2D slab type photonic crystal device is used. While two porous Si layers are formed as in Example 3, no oxide film coat is formed in the porous layers and the two porous layers are annealed simultaneously in this example. The Si crystal layer formed out of the upper porous layer by annealing is used to operate as core for an optical waveguide and the cavities formed in the lower porous layer at the same time are used to operate as lower clad. As a result, an air bridge type 2D slab type photonic crystal device is formed in this example.

Now, the method of preparing a photonic crystal device of this example will be described below by referring to FIGS. 14A through 14D.

Figure 14A:
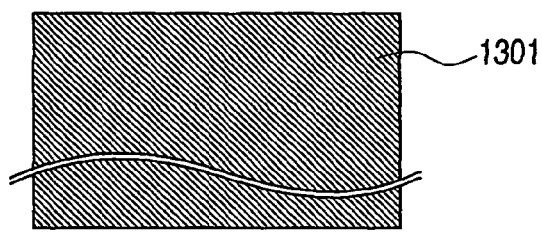
FIGS. 14A, 14B, 14C and 14D are schematic views of an air bridge photonic crystal of Example 4, showing the configuration thereof and a method of preparing the same.
Figure 14C:
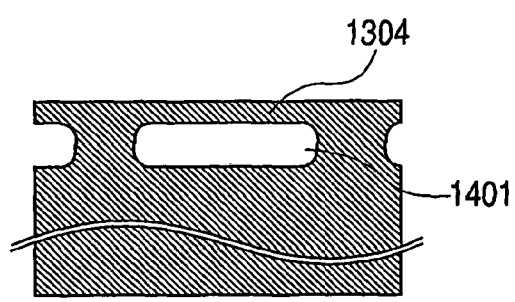
Figure 14B:
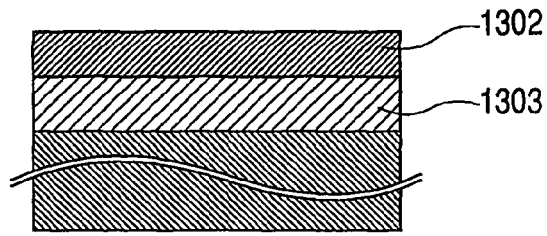

Firstly, two porous silicon layers 1302 and 1303 are formed by means of a two-stage anodization technique on an Si substrate 1301 as shown in FIG. 14A (FIG. 14B). The two porous silicon layers show respective porosities that are different from each other. More specifically, the porosity of the upper porous Si layer 1302 is made to be lower than the porosity of the lower porous Si layer 1303.

As in Example 2, a device showing a configuration as shown in FIG. 3 is used for the anodization. The porosity of each of the porous layers is controlled by the anodization current used.

Conditions for Anodization:
    starting wafer: $p^+Si$ (100) 0.01 Ωcm
    solution: HF, $C_2H_5OH$ and $H_2O$
    anodization current: 30 $mA/cm^2$ (upper layer), 150 $mA/cm^2$ (lower layer)

Thereafter, a hydrogen annealing operation is conducted on the conditions listed below.

Annealing Conditions:
    gas: 100% $H_2$
    temperature: 1,050° C.

As a result of hydrogen annealing, Si atoms in the surface and its vicinity of the upper porous Si layer 1302 moves to form a continuous crystal layer 1304 (FIG. 14C). The surface is smoothed to an atomic level to produce a high quality optical waveguide core structure where, particularly, unwanted scattering of light by the surface roughness of the order of 1/10 of the wavelength of light is suppressed. Since the lower porous Si layer 1303 shows a high porosity and hence is short of Si atoms, pores are coupled to one another to lower the surface energy so that consequently cavities 1401 are formed as shown in FIG. 14C. The phenomenon that cavities are formed as a result of hydrogen annealing is described in Japanese Patent Application Laid-Open No. 2000-144276. The cavities 1401 operate effectively as lower clad for confining light in an optical waveguide device.

Figure 14D:
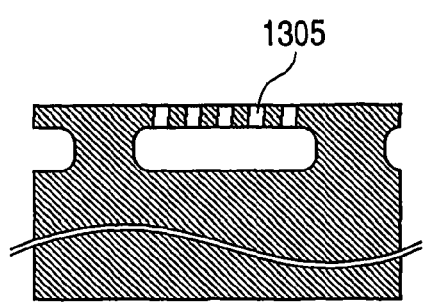

Then, a photolithography technique is applied to the crystal Si layer 1304 on the cavities 1401 to selectively remove silicon layer and form a periodic pattern of cylindrical holes (FIG. 14D). The etching operation for selectively removing the silicon layer is typically conducted on the following conditions.

Conditions for Processing the Silicon Layer:
    etching: reactive ion etching
    gas: $SF_6+CHF_3$ gas In this example, a cylindrical hole pattern showing a triangle lattice and including a defect waveguide or defect resonator similar to that of Example 1 is formed as periodic pattern 204. The diameter of cylindrical holes is about 0.3 μm, which is equal to about ¼ of the operating optical communication band of 1.5 μm, and the pattern cycle is about 0.7 μm.

As a result of using an air bridge structure, the crystal layer is brought to contact with air not only along the top surface but also along the bottom surface thereof so as to show a refractive index that is higher than that of the crystal layer when its bottom surface is held in contact with a porous layer so that light is confined more reliably. Additionally, since the crystal layer is formed not by means of epitaxial growth but by means of hydrogen annealing, the process is simple and does not use $SiH_4$ and other similar gas as in Example 3.

In the process of forming the upper porous Si layer 1302 as optical waveguide core layer 1304 by hydrogen annealing, any reduction in the film thickness is suppressed and the layer is formed reliably and stably when Si atoms are supplied in a vapor phase.

EXAMPLE 5

This example provides another example of preparing an air bridge type 2D slab type photonic crystal device. The crystal Si layer is formed by epitaxial growth and the underlying porous Si layer is processed by annealing to produce cavities, which are used as lower clad.

Now, the method of preparing a photonic crystal device of this example will be described below by referring to FIGS. 15A through 15F.

Figure 15A:
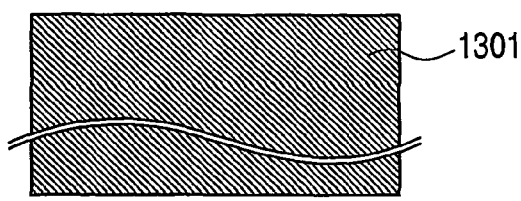
FIGS. 15A, 15B, 15C, 15D, 15E and 15F are schematic views of an air bridge photonic crystal of Example 5, showing the configuration thereof and a method of preparing the same.
Figure 15D:
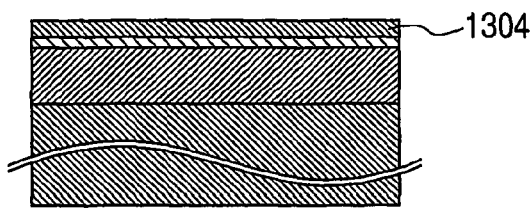
Figure 15B:
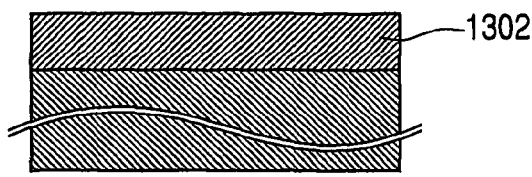

Firstly, a silicon layer 1302 having a porous structure is formed on an Si substrate 1301 as shown in FIG. 15A by anodization on the surface (FIG. 15B).

As in Example 2, a device showing a configuration as shown in FIG. 3 is used for the anodization.

Conditions for Anodization:
    starting wafer: $p^+Si$ (100) 0.01 Ωcm
    solution: HF, $C_2H_5OH$ and $H_2O$
    anodization current: 150 $mA/cm^2$ Then, the wafer is pre-baked in a hydrogen atmosphere to form a continuous crystal thin film structure 1501 on the surface to seal the pores on the surface of the porous Si layer 1302 (FIG. 15C). It is possible to supplement Si that is running short and reduce the crystal defects of the crystal thin film structure 1501 by supplying Si in a vapor phase.

Then, a crystal Si layer 1304 is added by epitaxial growth that starts from the surface of the crystal thin film structure 1501 (FIG. 15D).

Conditions for Epitaxial Growth:
vapor phase growth
temperature; 1,000° C.
gas: $SiH_4/H_2$
pressure: 700 Torr Thereafter, a hydrogen annealing operation is conducted on the following conditions.

Annealing Conditions:
gas: 100% $H_2$
temperature: 1,050° C.

Figure 15E:
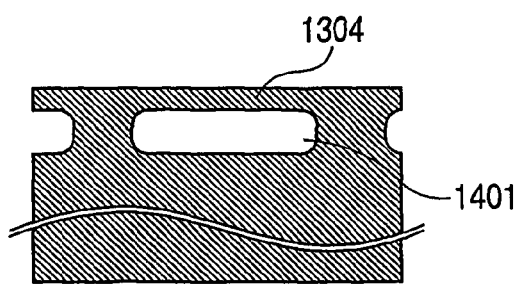
Figure 15C:
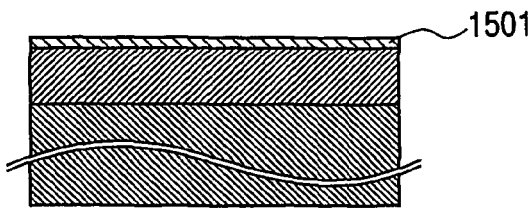

As a result of the hydrogen annealing, the porous Si layer 1302 turns into cavities 1401 (FIG. 15E). The principle underlying the phenomenon of producing cavities as described above in Example 4 also applies here. In short, Si atoms moves from the porous Si layer and its vicinity and void pores are coupled to one another to produce cavities 1401.

As a result, an optical waveguide is formed and the crystal layer 1304 operates as optical waveguide core while the cavities 1401 operate as lower clad layer there. Due to the hydrogen annealing, the wall surfaces of the cavities are smoothed to an atomic level to produce a high quality optical waveguide core structure in which unwanted scattering of light by the surface roughness of the order of $1/10$ of the wavelength of light is suppressed along the top surfaces of the cavities, or the interface of the cavity clad and the crystal layer optical waveguide.

Figure 15F:
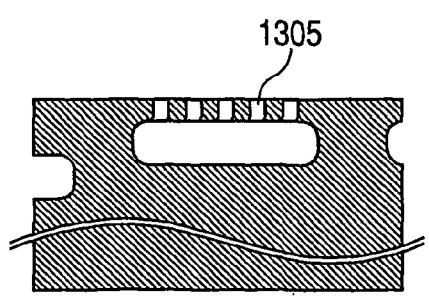

Then, as in Example 4, an air bridge type 2D slab type photonic crystal device is prepared as a result of forming a periodic pattern in the crystal Si layer 1304 that operates as optical waveguide core on the cavities 1401 (FIG. 15F).

In the process of sealing the void pores on the surface of the porous layer, the thin film crystal layer may be formed in a simplified way without supplying Si in a vapor phase and adding an Si crystal layer by means of epitaxial growth.

EXAMPLE 6

This example provides an active photonic crystal structure obtained by introducing an active medium into the clad layer of a 2D slab type photonic crystal device using a porous Si layer as clad and an epi-Si layer as core and a method of preparing such a structure.

Now, the method of preparing a photonic crystal device of this example will be described below by referring to FIGS. 16A through 16E.

Figure 16A:
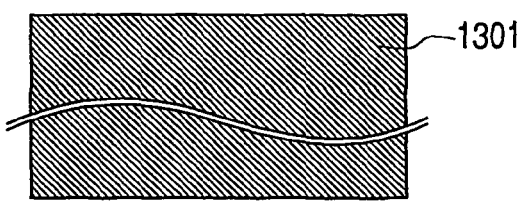
FIGS. 16A, 16B, 16C, 16D and 16E are schematic views of an active photonic crystal of Example 6, showing the configuration thereof and a method of preparing the same.
Figure 16D:
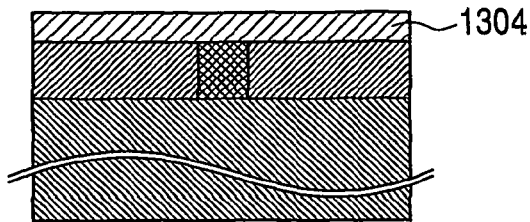
Figure 16B:
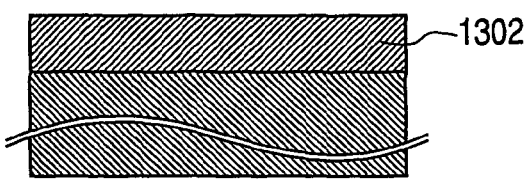
Figure 16E:
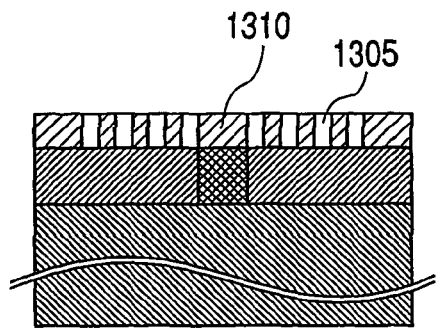

Firstly, a silicon layer 1302 having a porous structure is formed on an Si substrate 1301 as shown in FIG. 16A by anodization on the surface (FIG. 16B). A device showing a configuration as shown in FIG. 3 is used for the anodization.

Conditions for Anodization:
starting wafer: $p^+Si$ (100) 0.01 Ωcm
solution: HF, $C_2H_5OH$ and $H_2O$
anodization current: 150 mA/cm²

Figure 16C:
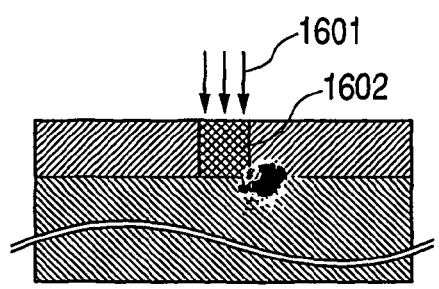

Then, accelerated Er ions 1601 are implanted into the porous Si layer 1302 to form an Er-doped region 1602 (FIG. 16C). If necessary, an annealing operation may additionally be conducted for the purpose of activation.

Then, a crystal Si layer 1304 is formed on the porous Si layer 1302 by epitaxial growth on the conditions listed below. It is important that this process is conducted in a hydrogen atmosphere so as to seal the pores on the surface of the porous layer and form a high quality epitaxial layer thereon.

Conditions for Epitaxial Growth:
vapor phase growth
temperature; 1,000° C.
gas: $SiH_4/H_2$
pressure: 700 Torr Thereafter, a photolithography technique is applied to the crystal Si layer 1304 to remove silicon layer and form a periodic pattern of cylindrical holes. The lower porous layer is left to remain there so as to operate as clad layer. The etching operation for selectively removing the silicon layer is typically conducted on the following conditions.

Conditions for Processing the Silicon Layer:
etching: reactive ion etching
gas: $Cl_2$ type gas A cylindrical hole pattern showing a triangle lattice and including a defect waveguide or defect resonator is formed as periodic pattern 204. The diameter of cylindrical holes is about 0.3 μm, which is equal to about ¼ of the gain wavelength zone of Er of 1 to 1.4 μm, or the operating waveform, and the pattern cycle is about 0.7 μm. The defect resonator 1310 is aligned with the Er-doped region 1602. With this arrangement, infrared rays transmitted through the Si photonic crystal and Er in the clad interact. Thus, it is possible to amplify infrared rays in the photonic crystal and produce laser oscillations by feeding back infrared rays to the photonic crystal defect resonator by means of optical switching using an nonlinear optical effect or by irradiating or introducing excited light with a wavelength of or close to 1 μm to the Er-doped regions 1602.

With the above-described process of this example, an active 2D slab type photonic crystal device containing an active medium in the clad layer is prepared.

While Er ions are used as active medium in this example, an organic fluorescent substance such as Alq3 or an inorganic fluorescent substance such as ZnS:Mn may alternatively be used. For example, an appropriate solution may be prepared and the porous Si layer may be dipped into the solution to adsorb such a substance into the void pores of the porous layer, utilizing the capillary phenomenon.

Additionally, the active medium may be selected from crystal materials GaAs, GaN, InGaN and AlInGaP. It is also possible to introduce such a substance into the void pores of the porous layer and subject it to crystal growth by means of a crystal growth system of MOCVD, CBE or MBE.

Figure 21A:
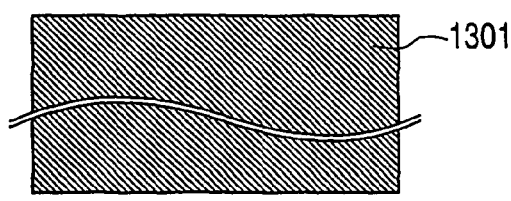
FIGS. 21A, 21B, 21C, 21D and 21E are schematic views of an active photonic crystal of Example 6, showing an alternative configuration thereof and a method of preparing the same.
Figure 21D:
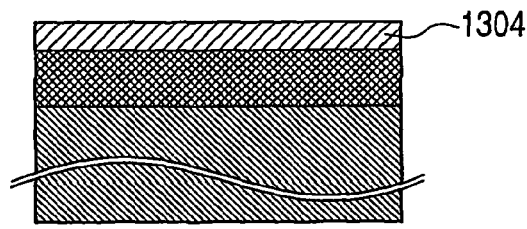
Figure 21B:
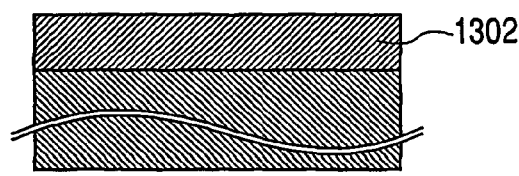
Figure 21E:
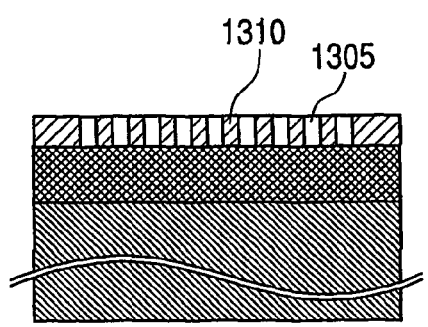
Figure 21C:
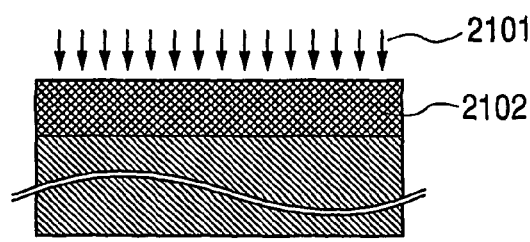

While the active medium is introduced into a part of the porous Si layer in this example, Er ions 2101 may alternatively irradiated onto the entire surface of the porous layer to produce a region 2102 that is doped with the active medium over the entire surface as shown in FIG. 21B. The remaining steps of the method of this example are same as those of FIGS. 16A through 16E.

EXAMPLE 7

In this example, an air bridge structure is formed by bringing an etching solution into contact with the porous Si layer of a 2D slab type photonic crystal as prepared in Example 2 by way of the cylindrical through holes and partly removing the porous Si layer.

Figure 5A:
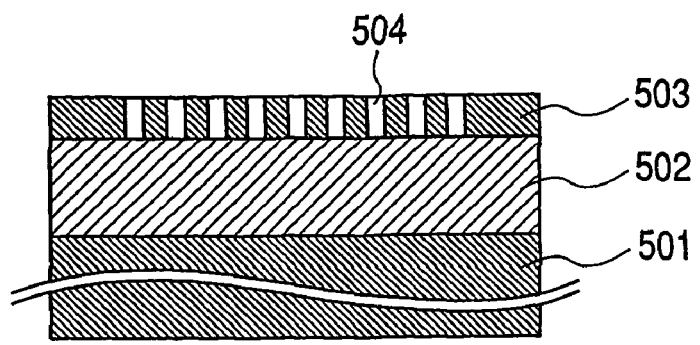
FIGS. 5A, 5B and 5C are schematic views of an air bridge type 2D slab type photonic crystal using porous Si of Example 7.

Now, the method of preparing a photonic crystal device of this example will be described below by referring to FIGS. 5A through 5C. The structure illustrated in FIG. 5A is same as that of the 2D slab photonic crystal prepared in Example 2 and obtained as a result of the step of FIG. 2D. More specifically, a porous Si layer 502 is formed on an Si seed substrate 501 and a single crystal Si layer 503 is formed thereon by epitaxial growth and subjected to a patterning operation to produce a photonic crystal pattern 504 there.

Figure 5B:
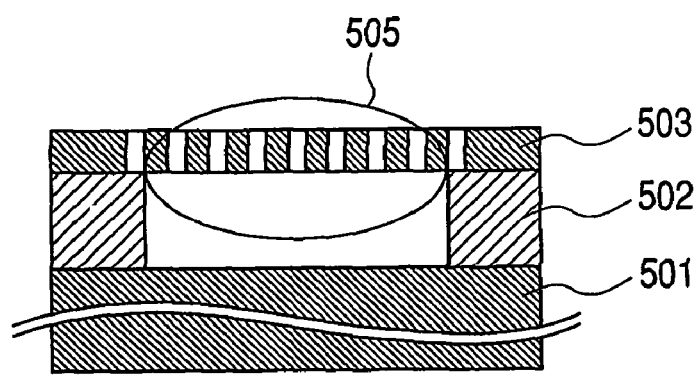
Figure 5C:
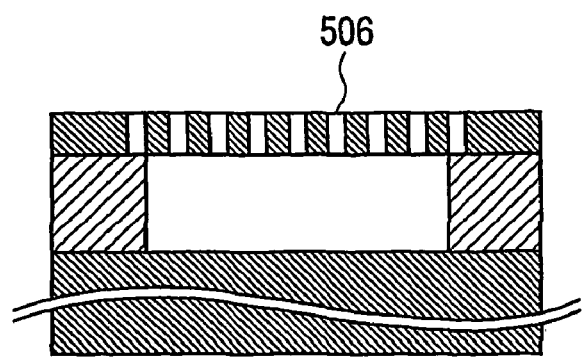

In this example, the lower porous layer 502 of the structure is partly removed by etching through the cylindrical holes formed in the single crystal layer to produce a cavity, which is used as clad layer (FIG. 5B).

Etching conditions:
  solution: $HF/H_2O$
  etching selectivity ratio:
  crystal layer:porous layer =1:100,000

With the method of this example, it is possible to produce a cavity right under the cylindrical holes.

Then, hydrogen annealing is conducted on the following conditions. As a result, the front surface, the lateral walls and the rear surface (cavity side of the air bridge) of the single crystal Si layer 505 that carries the pattern are smoothed.

Hydrogen Annealing Conditions:
  gas: 100% $H_2$
  temperature: 1,050° C.

The propagation loss is reduced when the smoothed photonic crystal is used for a waveguide, whereas a high Q value is obtained as a result of suppressing the loss when the smoothed photonic crystal is used for a resonator.

EXAMPLE 8

This example provides a method of preparing a 2D slab type photonic crystal device, using a porous Ge layer as clad and an epi-GaAs layer as core.

Now, the method of preparing a photonic crystal device of this example will be described below by referring to FIGS. 6A through 6D.

Figure 6A:
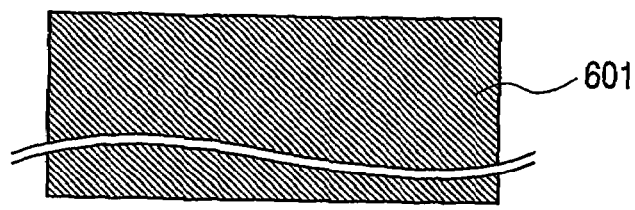
FIGS. 6A, 6B, 6C and 6D are schematic views of a 2D slab type photonic crystal using a porous Ge clad and a GaAs core of Example 8, showing the configuration thereof.
Figure 6B:
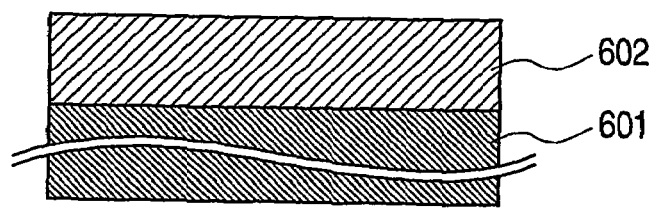
Figure 6C:
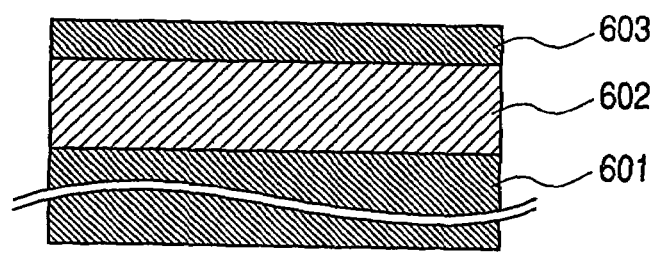
Figure 6D:
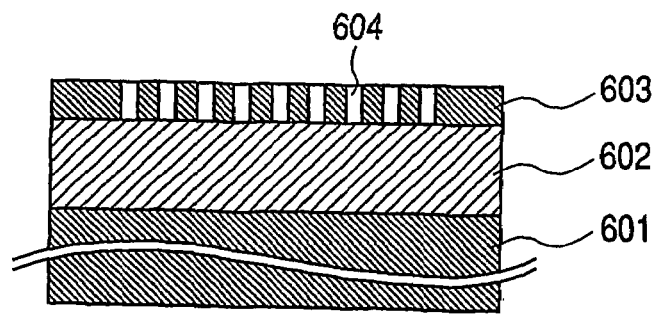

Firstly, a Ge layer 602 having a porous structure is formed on a Ge substrate 601 as shown in FIG. 6A by anodization (FIG. 6B). A device showing a configuration as shown in FIG. 3 may be used for the anodization. The process of anodization becomes less expensive when a number of wafers are treated on a batch basis by means of a device as shown in FIG. 4.

Conditions for Anodization:
  starting wafer: $p^+Ge(100)$ 0.01 Ωcm
  solution: a mixed solution of HF, $C_2H_5OH$ and $H_2O$
  anodization current: 100 $mA/cm^2$ Then, an epi-GaAs layer 603 is formed on the porous Ge layer 602 by epitaxial growth. Thereafter, a periodic pattern 604 is formed in the Epi-GaAs layer 603 by means of a photolithography technique.

In this example, a cylindrical hole pattern showing a triangle lattice and including a defect waveguide or defect resonator similar to that of Example 1 is formed as periodic pattern 604. The diameter of cylindrical holes is about 0.3 μm, which is equal to about ¼ of the operating optical communication band of 1.5 μm, and the pattern cycle is about 0.7 μm.

Meanwhile, beside photolithography described above as patterning technique of this example, nano-imprinting that is less expensive, X-ray lithography that provides a higher resolution, ion beam lithography, EB lithography or optical near field lithography may selectively be used depending on the application of the device.

Thus, a 2D slab type photonic crystal device that does not require any bonding operation is prepared with the method of this example.

Since GaAs, which is a direct transition type optical semiconductor, is used for the core layer, the device of this example can be used for emitting light by excitation of light or for a switching device that utilizes the optical nonlinearity of the device. Thus, it is possible to produce highly sophisticated devices by using the method of this example.

While GaAs is used in this example, any other crystal material may alternatively be used without problem so long as the lattice constant and the linear expansion coefficient of the material are close to those of Ge.

EXAMPLE 9

Figure 7A:
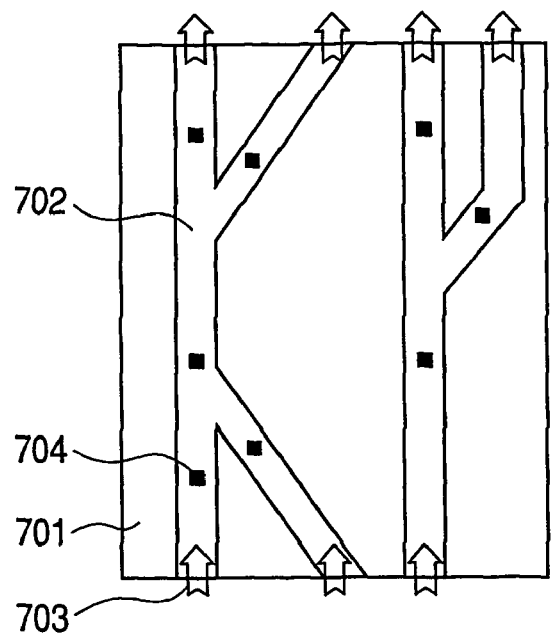
FIGS. 7A, 7B and 7C are schematic views of a μTAS laser sensor system using a 2D photonic crystal of Example 9, showing the configuration thereof.
Figure 7B:
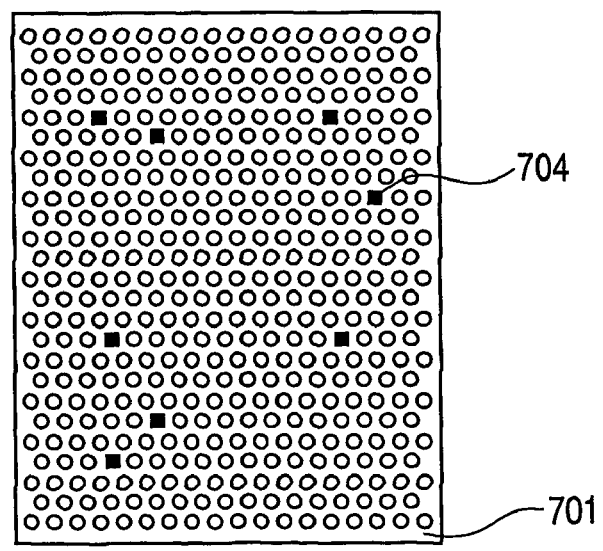
Figure 7C:
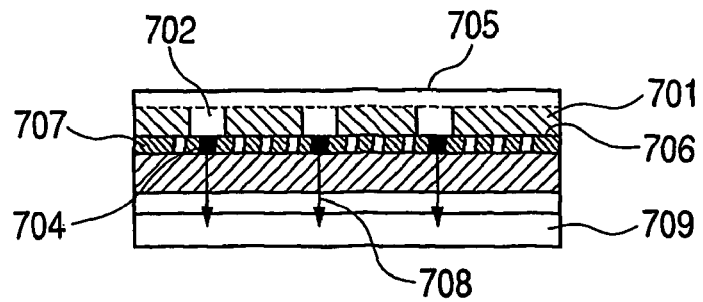

Now, the ninth example of the present invention will be described by referring to FIGS. 7A through 7C. FIGS. 7A through 7C illustrate a μTAS (micro-total analysis system) sensor system using a photonic crystal according to the invention.

FIG. 7A is a schematic illustration of the flow channel system of a μTAS and photonic crystal laser sensors, showing their positional relationship. As shown in FIG. 7A, flow channels 702 are formed in a flow channel substrate 701 and liquid 703 that contains information to be detected is made to flow there. As shown in FIG. 7A, the flow channel system may have an appropriate configuration so as to make it adapted to agitation, reaction or some other operation specific to μTAS as well as branches, junctions and so on. It will be seen from the perspective illustration that photonic crystal laser sensors 704 are arranged immediately below the flow channels.

The photonic crystal lasers of this example are prepared by forming point defect type resonators, using 2D slab type photonic crystal, and arranging laser mediums at the point defects, which are excited by a light exciting means (not shown).

Figure 12:
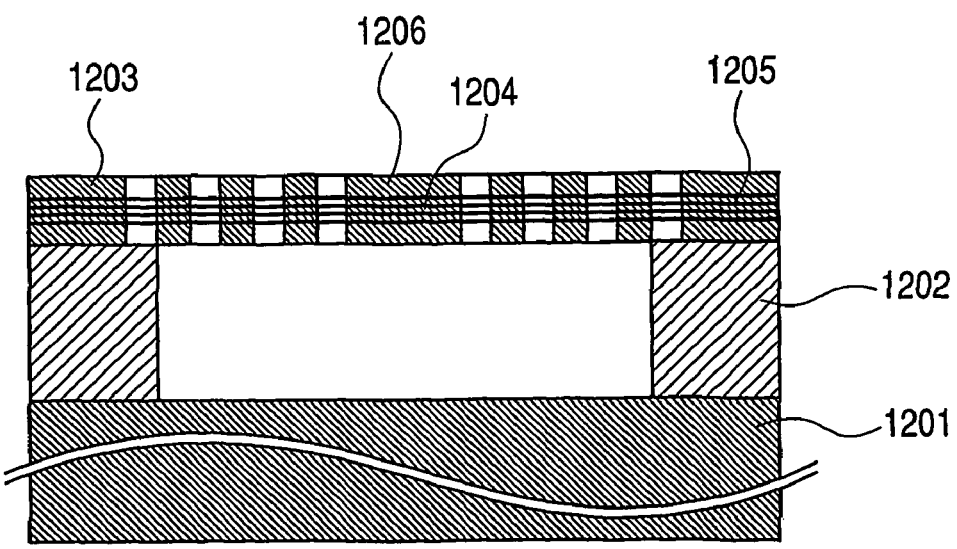
FIG. 12 is a schematic illustration of a laser sensor system using photonic crystal of Example 9, showing the configuration thereof.

FIG. 12 schematically illustrates exemplary photonic crystal lasers. As shown in FIG. 12, a porous Ge layer 1202 is formed on a Ge substrate 1201 as clad layer and then a GaAs layer is formed thereon as core layer by epitaxial growth. Then, a multiple quantum well structure 1205 is formed thereon by using a ternary compound of AlGaAs as active layer 1204, or a laser medium layer. Subsequently, the structure 1205 is subjected to a patterning operation to form a periodic cylindrical hole pattern of photonic crystal that includes a defect resonator part 1206 and then an air bridge structure is produced.

Of photonic crystal lasers having such a configuration, the threshold values, the conditions of oscillation and the state of oscillation react very sensitively to the surrounding environment so that it can be used as micro-laser sensor. The state of laser oscillation of the photonic crystal laser sensors of this example changes very sensitively as a function of the concentration of the substances contained in the fluid flowing through the fluid paths, the refractive index, the temperature and the pressure of the fluid and other factors so that it is possible to detect the changes in the fluid by detecting the state of the laser beam output. As shown in FIG. 7C, the laser beam output is detected by the lowermost light receiving layer 709 and the state of oscillation of each laser sensor is detected.

When the laser is excited by injecting an electric current, the state of oscillation of the laser sensor can be observed by detecting the changes in the electric current that is being injected instead of detecting the laser beam output.

FIG. 7C is a schematic cross sectional view of the sensor system of this example. As described above, flow channels 702 are formed in the flow channel layer 701 and a cover layer 705 is formed thereon to close the flow channels 702 at the tops thereof. The flow channel 702 is also closed at the bottoms thereof by a thin film 706 and photonic crystal lasers 704 are arranged in contact with the thin film 706. The thin film 706 has a thickness substantially equal to the oscillation wavelength of the photonic crystal lasers so that evanescent light from the photonic crystal laser resonators reaches the fluid 703 in the fluid paths 702. At the same time, the designed loss of the laser resonators is made very close to the conditions to be met for oscillation. In other words, a slight change in the fluid can stop or trigger oscillation.

Thus, it is possible to produce a μTAS sensor system by using a photonic crystal and a method of preparing the same according to the invention.

EXAMPLE 10

A 2D slab type photonic crystal is applied to a sensor in this example. Through holes are formed in the single crystal layer of a photonic crystal device to show a periodic pattern and utilized as flow channels.

The sensor will be described by referring to FIGS. 17A through 17D, 20A and 20B.

FIGS. 17A and 17B schematically illustrate the basic steps of the method of preparing a sensor of this example. Firstly, a part of a surface of an Si wafer 1301 that makes a rectangular region 1701 and an optical waveguide region (not shown) extending in an intra-planar direction is subjected to an operation of anodization to make it show pores (FIG. 17A).

Then, the void pores exposed to the surface of the porous layer are pre-baked in an hydrogen atmosphere to seal them and subsequently a crystal Si layer 1702 is formed on the surface of the Si wafer by epitaxial growth (FIG. 17B).

Thereafter, a photonic crystal pattern 1305 and an optical waveguide pattern 1703 are formed in the crystal Si layer by patterning (FIG. 17C).

Then, etchant is made to infiltrate through the plurality of cylindrical holes formed as as pattern in the photonic crystal in order to remove the porous Si in the rectangular region 1701 below the photonic crystal region by selective wet etching and produce a flow channel 1704 (FIG. 17D).

The optical device/flow channel structure 1801 prepared in this way is then bonded to an upper flow channel structure 1802 made of PDMS (polydimethylsiloxane) and prepared separately as shown in FIG. 18A to produce a sensor having a flow-through structure (FIG. 18B).

The transmission characteristics of the photonic crystal 1305 change depending on the type and the properties of the object fluid that is guided by the flow channels 1803 and 1704 to flow through the cylindrical holes of the photonic crystal. It is possible to detect the object substance by optical spectrum observation through the optical waveguide 1703.

Alternatively, through holes may be formed at an end of the flow channel 1704 from the Si layer as shown in FIG. 19A. Then, through holes can be formed simultaneously with the patterning operation for the photonic crystal and the optical waveguide. With this arrangement, it is possible to form an inflow channel 1803 and an outflow channel 1903 in a same layer as viewed in the multilayer direction to a great advantage for forming a system that comprises such a sensor and is connected to a so-called μ-TAS system.

Still alternatively, it is also possible to produce a flow through structure having cylindrical holes formed through the photonic crystal 1305 and through holes formed from the rear surface of the Si substrate 2001 of a photonic crystal device, in which a porous Si layer 2004 is formed on the entire surface of the substrate 2001 as shown in FIG. 20A. This arrangement provides a first advantage that the structure is very strong because the thin film of the photonic crystal is supported by the porous layer and a second advantage that the flow through of the device can be controlled in various different ways to correspond to the properties of the object fluid by controlling the porosity and the pore diameter of the porous layer. For example, when detecting protein in a solution, the size of the void pores is made to of the order of the size of the object protein so as to prevent protein, or solute, from passing through the porous layer and encourage protein to adhere to the void pores in the clad layer and the cylindrical holes in the photonic crystal.

Thus, as described above, it is possible to prepare a flow through type sensor by using a photonic crystal device having a porous layer according to the invention.

While PDMS is used as material for forming the upper flow channel structure in this example, it may be needless to say that some other appropriate material such as Si, quartz or glass may alternatively be used.

EXAMPLE 11

This example provides an optical device, which is typically a fine wire waveguide, formed by using porous silicon.

Figure 8A:
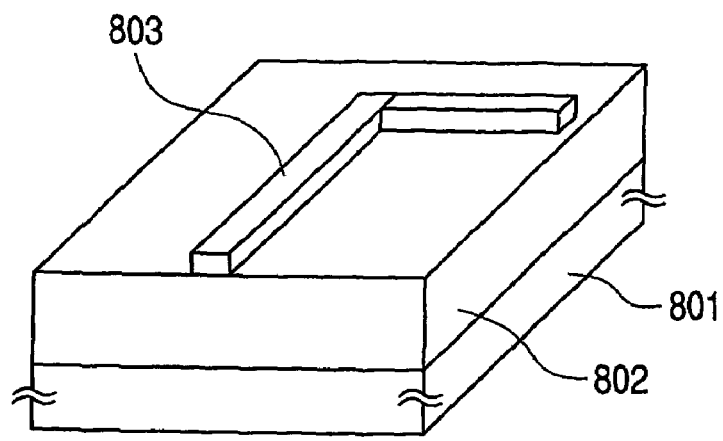
FIGS. 8A, 8B and 8C are schematic views of an Si fine wire waveguide device using porous Si for the clad layer of Example 11, showing the configuration thereof.
Figure 8B:
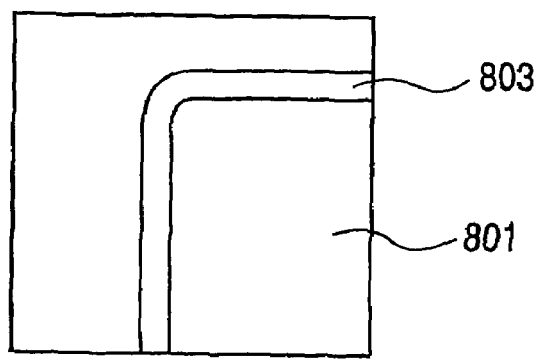
Figure 8C:
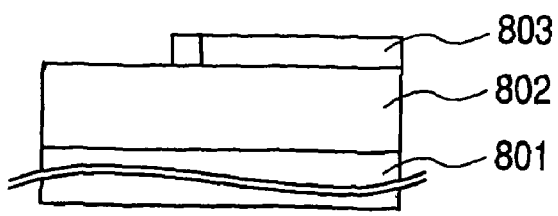

This example will be described below by referring to FIGS. 8A through 8C. Referring to FIGS. 8A through 8C, a porous silicon layer 802 is formed by anodization on a silicon substrate 801, which is a seed wafer, and a single crystal silicon layer 803 is formed further thereon by epitaxial growth as in Example 1.

A fine wire pattern is formed from the single crystal silicon layer 803 to produce a waveguide by means of a photolithography technique of applying resist and conducting a patterning operation by means of an exposure system, which is followed by an etching operation. The porous silicon layer 802 is subjected to selective etching. More specifically, the lateral walls of the pores of the porous silicon are coated by a very thin oxide film and the silicon epitaxial layer and the porous layer, in which the lateral walls of the pores are covered by an oxide film coat, are subjected to selective etching, using a reactive ion etching (RIE) technique. The selectivity of the etching rises and, at the same time, the refractive index of the porous layer falls when a relatively thick oxide film coat is used.

The fine wire surface and the lateral walls are smoothed by hydrogen annealing on the following conditions.

Annealing Conditions:
gas: 100% $H_2$
temperature: 1,050° C.

As a result of hydrogen annealing, the fine wire surface and the lateral walls are smoothed to an atomic level. Particularly, the structure that generates unwanted scattering Of light by the surface roughness of the order of ⅒ of the wavelength of light is eliminated so that it is possible to remarkably suppress the optical loss as an important characteristic feature of fine wire waveguide. When an optical resonator is produced by forming an annular fine wire waveguide (see Kawakami et al., ibid, p. 262), the Q value, which indicates an important characteristic of the resonator, is raised to by turn improve the wavelength filtering characteristic and the laser oscillation threshold value of the device realized by using the resonator.

Thus, a silicon fine wire waveguide whose surface is smoothed and optical loss is suppressed is formed to use the low refractive index porous silicon layer as lower clad.

While a photolithography technique is used for the patterning operation in this example, nano-imprinting that is less expensive, X-ray lithography that provides a higher resolution, ion beam lithography, EB lithography or optical near field lithography may selectively be used depending on the application of the device.

EXAMPLE 12

This example provides another optical device, which is also a fine wire waveguide, formed by using porous silicon.

Figure 9A:
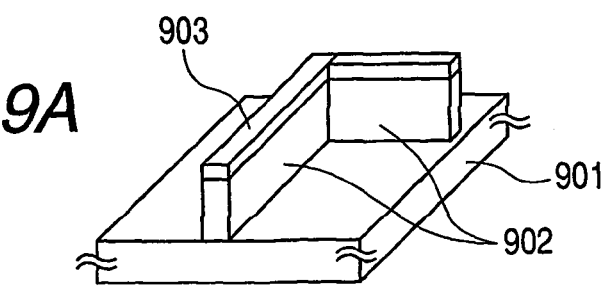
FIGS. 9A, 9B and 9C are schematic views of an Si fine wire waveguide device using porous Si for the clad layer of Example 12, showing the configuration thereof.
Figure 9B:
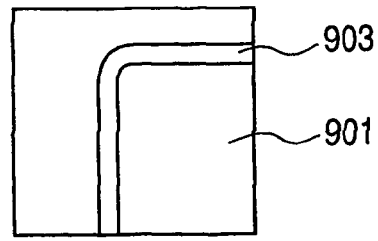
Figure 9C:
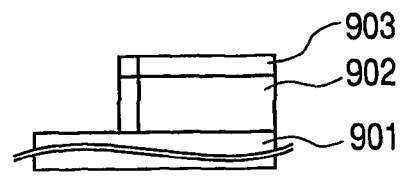

This example will be described below by referring to FIGS. 9A through 9C. Referring to FIGS. 9A through 9C, a porous silicon layer 902 is formed by anodization on a silicon substrate 901, which is a seed wafer, and a single crystal silicon layer 903 is formed further thereon by epitaxial growth as in Example 1. A fine wire pattern is formed from the porous silicon layer and the single crystal silicon layer to produce a waveguide by means of a photolithography technique of applying resist and conducting a patterning operation by means of an exposure system, which is followed by an etching operation.

The fine wire surface and the lateral walls are smoothed by hydrogen annealing on the following conditions.

Annealing Conditions:
  gas: 100% $H_2$
  temperature: 1,050° C.

As a result of hydrogen annealing, the fine wire surface and the lateral walls are smoothed to an atomic level. Particularly, the structure that generates unwanted scattering of light by the surface roughness of the order of $\frac{1}{10}$ of the wavelength of light is eliminated so that it is possible to remarkably suppress the optical loss as an important characteristic feature of fine wire waveguide. When an optical resonator is produced by forming an annular fine wire waveguide (see Kawakami et al., ibid, p. 262), the Q value, which indicates an important characteristic of the resonator, is raised to by turn improve the wavelength filtering characteristic and the laser oscillation threshold value of the device realized by using the resonator.

Thus, a silicon fine wire waveguide whose surface is smoothed and optical loss is suppressed is formed to use the low refractive index porous silicon layer as lower clad.

While a photolithography technique is used for the patterning operation in this example, nano-imprinting that is less expensive, X-ray lithography that provides a higher resolution, ion beam lithography, EB lithography or optical near field lithography may selectively be used depending on the application of the device.

Figure 10:
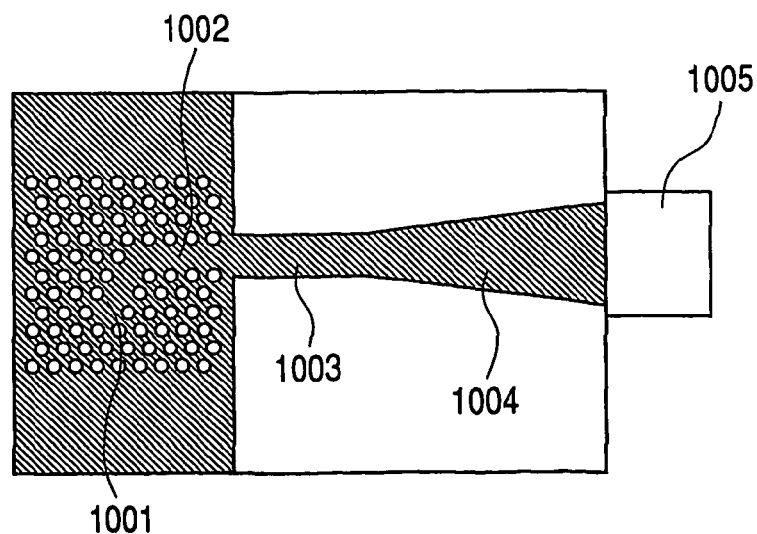
FIG. 10 is a schematic illustration of an alternative Si fine wire waveguide device using porous Si for the clad layer of Example 12, showing the configuration thereof.

It may be needless to say that a fine wire waveguide of this example can be combined with an above described 2D slab type photonic crystal in a hybrid mode. For example, as schematically shown in FIG. 10, a resonator having a minimum mode volume may be connected to a waveguide by means of point defects and line defects of photonic crystal while the line defect waveguide may be connected to a fine wire waveguide of this example and the diameter of the fine wire waveguide may be gradually increased in an adiabatic manner to connect it to an external optical fiber. Various other combinations may also be conceivable depending on the object and the application.

Figure 22C:
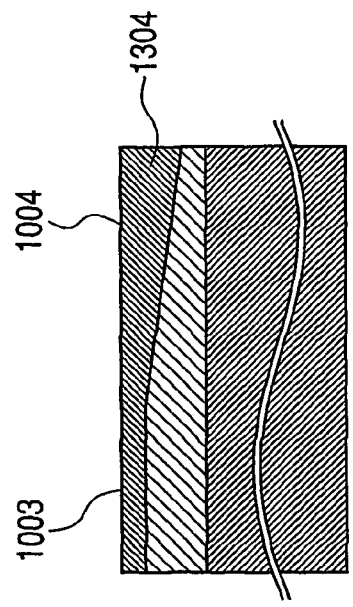
Figure 22D:
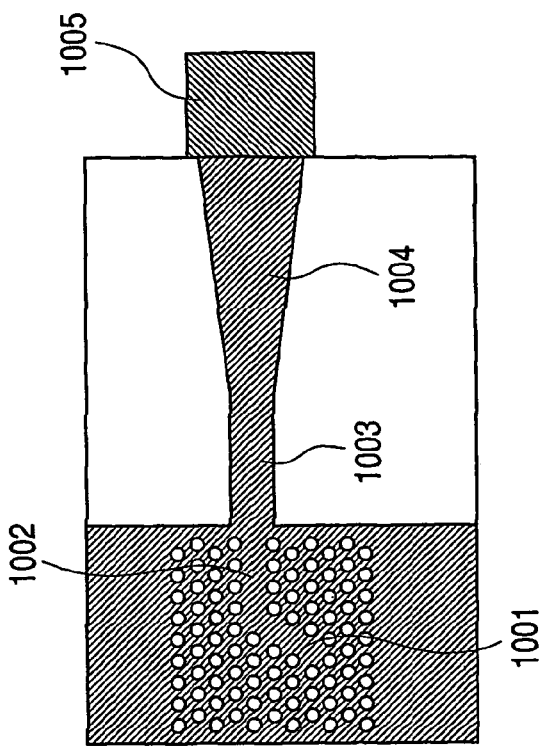
Figure 22A:
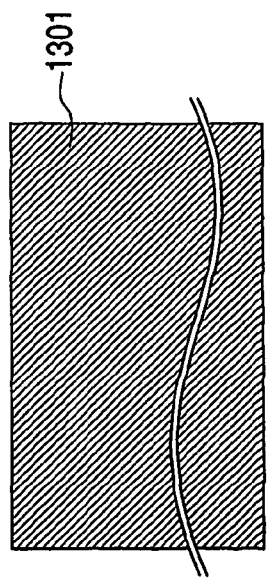
Figure 22B:
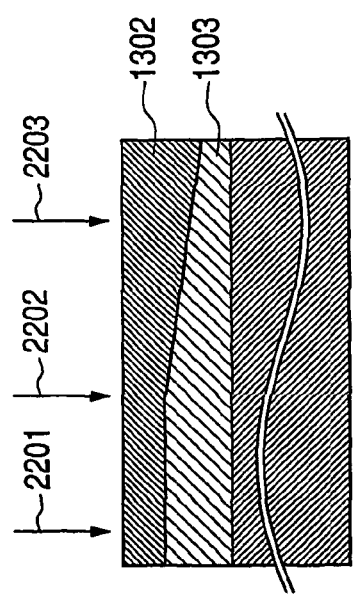

An adiabatically mode-transferred waveguide can be realized more appropriately by a method according to the invention. For example, as shown in FIGS. 22A through 22D, two porous crystal layers 1302 and 1301 may be made to show different thicknesses by changing with time the respective anodization currents for different positions 2201, 2202 and 2203 as viewed in an intra-planar direction (FIG. 22B). Particularly, it is possible to produce an inclination in a span between two positions 2202 and 2203 as viewed in the intra-planar direction. Then, an optical waveguide core whose thickness changes in an adiabatic manner can be obtained from it by hydrogen annealing. As shown in FIG. 22C and FIG. 22D, which is a corresponding schematic plan view, it is possible to produce a waveguide that is also adiabatic in a direction perpendicular to the plane. It is also possible to change the ratio of the thicknesses of two porous layers by irradiating light showing a luminance distribution including an inclination for intra-planar positions instead of changing the anodization currents at intra-planar positions due to the boosting effect of anodization that is attributable to photo carriers.

EXAMPLE 13

This example provides an optical device formed by using porous silicon and transforming the porous silicon layer into a porous $SiO_2$ layer by oxidation.

Figure 11:
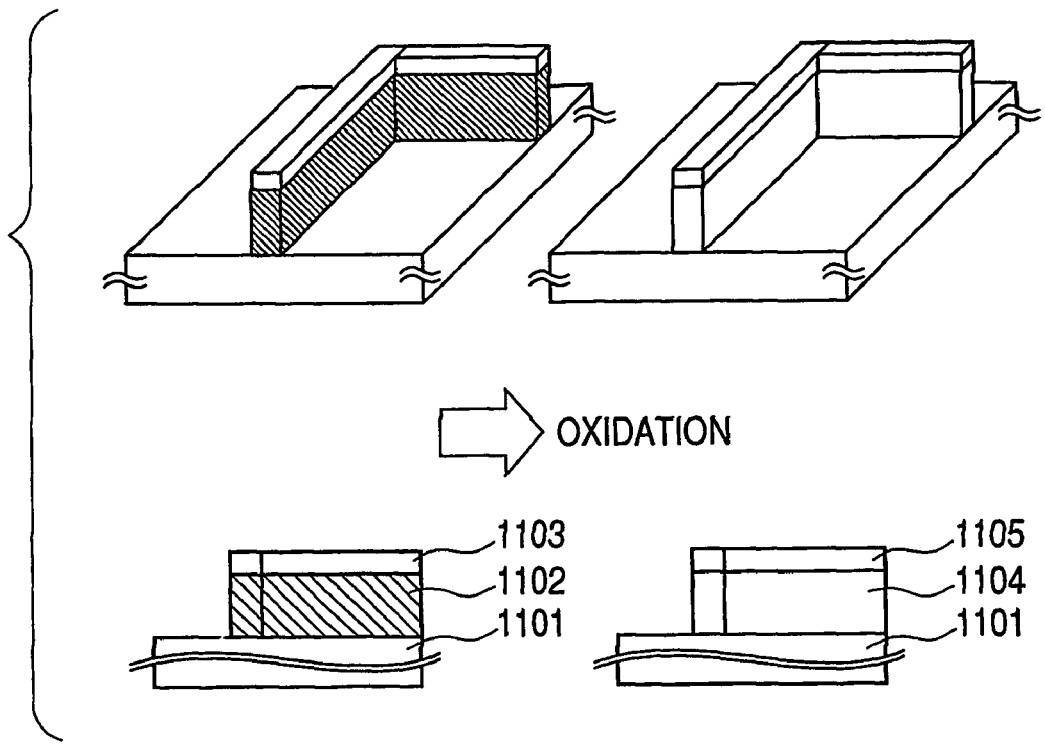
FIG. 11 is a schematic illustration of a surface oxidized Si fine wire waveguide device using porous $SiO_2$ obtained by oxidation for the clad layer of Example 13, showing the configuration thereof.

Now, this device will be described by referring to FIG. 11. FIG. 11 is a schematic illustration of the optical device of this example, showing a manufacturing process thereof. In FIG. 11, the upper two views are perspective views and the lower two views are lateral views. The left two views of FIG. 11 illustrate the device having a porous silicon layer 1102 formed on a silicon substrate 1101, which is a seed wafer, by anodization as in Example 7 and a single crystal silicon layer 1103 formed by epitaxial growth. A fine wire pattern is formed from the porous silicon layer and the single crystal silicon layer to produce a waveguide by means of a photolithography technique of applying resist and conducting a patterning operation by means of an exposure system, which is followed by an etching operation.

The fine wire surface and the lateral walls are smoothed by hydrogen annealing as in Example 7.

In this example, the specimen is further oxidized on the following conditions for oxidation.

Conditions for Oxidation:
  gas: $O_2/H_2$
  temperature: 1,050° C.

The right views in FIG. 11 show the fine wire waveguide obtained after the oxidation. While the non-porous crystal silicon layer and the underlying porous silicon layer of the fine wire waveguide are oxidized as a result of oxidation, the Si in the porous layer is oxidized at a rate that is about a hundred times greater than the rate of oxidation of the non-porous crystal Si. Thus, it is possible to oxidize almost all the porous silicon layer (1104 in FIG. 11) and only the surface of the non-porous crystal silicon layer (1105 in FIG. 11) by regulating the duration of the oxidation process. As a result, the bottom, the lateral surfaces and the top surface of the fine wire optical waveguide are surrounded by a thermal oxidation layer showing a uniform refractive index and light is confined by an air layer and a porous $SiO_2$ layer that further surround the waveguide with a sufficient thickness. The interface between the silicon and the $SiO_2$ of the fine wire waveguide that is produced by the oxidation is smooth and effective for suppressing unwanted light loss due to scattering because the silicon is subjected to hydrogen annealing in advance. Thus, an excellent optical waveguide is formed directly on a silicon substrate without using an expensive SOI substrate.

A legend of the reference symbols in the drawings is shown below.
101: Si seed substrate
102: porous Si layer
103: epi-grown Si layer
104: photonic crystal pattern
105: line defect waveguide
106: point defect resonator
107: point defect resonator
201: Si seed substrate
202: porous Si layer
203: epi-grown Si layer
204: photonic crystal pattern
301: Si substrate for preparing photonic crystal
302: HF solution
303: O-ring
304: Pt-made surface electrode
305: lower support body
306: upper support body
307: anode
308: Pt-made mesh electrode
309: cathode
401: Si substrate for preparing photonic crystal
402: piping for vacuum chuck
403: wafer holder
404: HF solution tank
405: HF solution
406: anode
407: cathode
501: Si seed substrate
502: porous Si layer
503: epi-grown Si layer
504: photonic crystal pattern
505: air bridge section
506: Si plane surface after annealing
601: Ge seed substrate
602: porous Ge layer
603: epi-grown GaAs layer
604: photonic crystal pattern
701: flow channel substrate
702: flow channel
703: fluid
704: photonic crystal laser sensor
705: cover layer
706: thin film
707: photonic crystal layer
708: laser beam output
709: light receiving layer
801: Si seed substrate
802: porous Si layer
803: epi-grown Si fine wire waveguide
901: Si seed substrate
902: porous Si layer
903: epi-grown Si fine wire waveguide
1001: photonic crystal defect resonator
1002: photonic crystal line defect waveguide
1003: Si fine wire waveguide
1004: tapered section of Si fine wire waveguide
1005: external optical waveguide/optical fiber system
1101: Si seed substrate
1102: porous Si layer
1103: epi-grown Si fine wire waveguide
1104: porous $SiO_2$ layer (thermally oxidized $SiO_2$)
1105: epi-grown Si fine wire waveguide with thermally oxidized $SiO_2$ film
1201: Ge seed substrate
1202: porous Ge layer
1203: GaAs crystal layer
1204: active layer
1205: multiple quantum well
1206: defect resonator part
1301: Si substrate
1302: upper porous Si layer
1303: lower porous Si layer
1304: optical waveguide core Si crystal layer
1305: photonic crystal pattern
1401: lower clad cavity
1501: crystal thin film structure
1601: Er ion
1602: Er-doped region
1701: porous Si region
1702: epitaxial Si layer
1703: optical waveguide
1704: flow channel cavity
1801: optical device/flow channel structure
1802: upper flow channel structure
1803: upper flow channel
1901: optical device/flow channel structure
1902: flow channel through pore
1903: discharge flow channel
2001: optical device/flow channel structure
2002: lower flow channel structure
2003: lower flow channel
2004: porous Si layer
2101: active medium
2102: porous crystal layer including active medium
2201: intra-planar position 1
2202: intra-planar position 2
2203: intra-planar position 3
2301: partial wafer
2302: optical waveguide device pattern
2303: bar wafer
2304: optical waveguide device This application claims priority from Japanese Patent Application Nos. 2003-305486 filed Aug. 28, 2003 and 2004-244686 filed Aug. 25, 2004, which are hereby incorporated by reference herein.

The invention claimed is:

1. An optical device comprising a substrate, a porous layer laid on the substrate having a pore diameter smaller than the wavelength of light and a crystal layer laid on the porous layer showing a refractive index greater than that of the porous layer.

2. The device according to claim 1, characterized in that said crystal layer forms a waveguide for propagating light in an in-plane direction.

3. The device according to claim 1, characterized in that said crystal layer shows a periodic refractive index distribution in the layer.

4. The device according to claim 1, characterized in that said crystal layer has line defects or point defects arranged in the periodic refractive index distribution in the layer.

5. The device according to claim 4, characterized in that said crystal layer forms an optical waveguide along said line defects.

6. The device according to claim 4, characterized in that said crystal layer forms an optical resonator for localizing light around said point defects.

7. The device according to claim 6, characterized in that said optical resonator is a laser resonator.

8. The device according to claim 1, characterized in that said crystal layer shows a fine wire pattern and forms a waveguide.

9. The device according to claim 8, characterized in that said crystal layer shows a fine wire pattern and forms a waveguide with said porous layer.

10. The device according to claim 1, characterized in that said crystal layer includes an air bridge structure formed between the crystal layer and the substrate that is devoid of a porous layer.

11. The device according to claim 1, characterized in that said crystal layer having a large refractive index shows a thickness that varies depending on the position on said substrate in an intra-planar direction.

12. The device according to claim 1, characterized in that an active medium is introduced into said porous layer.

13. The device according to claim 1, characterized in that said porous layer is a porous silicon layer, a porous silicon layer having its surface coated with silicon oxide or a porous silicon oxide layer and said crystal layer is a single crystal layer.

14. The device according to claim 1, characterized in that said porous layer is a porous germanium layer and said crystal layer is a crystal GaAs layer.

15. A method of manufacturing an optical device characterized by comprising a step of forming a porous layer having a pore diameter smaller than the wavelength of light on the surface of a substrate and a step of forming a crystal layer showing a refractive index greater than that of the porous layer on the porous layer.

16. The method according to claim 15, characterized in that
said step of forming a porous layer is a step of forming a porous layer by anodization on the surface of the substrate.

17. The method according to claim 15, characterized by further comprising a step of annealing the porous layer in a hydrogen atmosphere and forming a cavity in the porous layer.

18. The method according to claim 15, characterized in that
said step of forming a porous layer is a step of forming two porous layers showing respective porosities that are different from each other by means of two-stage anodization.

19. The method according to claim 18, characterized by further comprising a step of annealing the porous layer showing the lower porosity in a hydrogen atmosphere and forming a crystal layer.

20. The method according to claim 19, characterized in that
an oxide film coat is formed on the lateral walls of the pores of the porous layer showing the higher porosity before said step of annealing and forming a crystal layer.

21. The method according to claim 18, characterized by further comprising a step of annealing the porous layer showing the higher porosity in a hydrogen atmosphere and forming a cavity.

22. The method according to claim 15, characterized in that
said step of forming a crystal layer is a step of forming a crystal layer by epitaxial growth.

23. The method according to claim 22, characterized by further comprising a step of oxidizing the surface of the porous layer before said step of forming a crystal layer by epitaxial growth.

24. The method according to claim 15, characterized by further comprising a step of forming through holes in said crystal layer.

25. The method according to claim 24, characterized by further comprising a step of etching and removing the porous layer under the crystal layer by way of the through holes.

26. The method according to claim 25, characterized by further comprising a step of annealing the crystal layer in a hydrogen atmosphere and smoothing the front surface and the rear surface of the crystal layer and the lateral walls of the through holes after said step of etching and removing said porous layer.

27. The method according to claim 15, characterized by further comprising a step of patterning the crystal layer and etching and removing it to form a waveguide.

28. The method according to claim 27, characterized by further comprising a step of forming an oxide film coat on the lateral walls of the pores of the porous layer before said step of forming a waveguide.

29. The method according to claim 15, characterized by further comprising a step of patterning the crystal layer and the porous layer and etching and removing them to form a waveguide.

30. The method according to claim 29, characterized by further comprising a step of oxidizing the porous layer under the crystal layer after said step of forming a waveguide.

31. The method according to claim 30, characterized by further comprising a step of annealing the waveguide in a hydrogen atmosphere and smoothing the surface and the lateral walls of the waveguide after said step of forming a waveguide.

32. The method according to claim 15, characterized by further comprising a step of introducing an active medium into the porous layer after forming said porous layer.

33. The method according to claim 15, characterized by further comprising a step of cleaving along the crystal surface bearing of the substrate.

34. A sensor characterized by comprising a porous layer having a pore diameter smaller than the wavelength of light, a crystal layer showing a refractive index greater than that of the porous layer and laid on the porous layer, a region in the crystal layer showing a periodic distribution of refractive index, a flow channel for flowing fluid in the vicinity of the region and means for irradiating light onto the region and detecting light emitted from the region.

35. The sensor according to claim 34, characterized in that said region showing a distribution of refractive index is located outside said flow channel and arranged in such a way that evanescent waves of light propagating through the crystal layer in said region reaches the flow channel.

36. The sensor according to claim 34, characterized in that said region showing a distribution of refractive index is formed by through holes arranged in said substrate to form a periodic pattern and the through holes take part of said flow channel.

* * * * *

UNITED STATES PATENT AND TRADEMARK OFFICE
CERTIFICATE OF CORRECTION

PATENT NO. : 7,171,095 B2
APPLICATION NO. : 10/545157
DATED : January 30, 2007
INVENTOR(S) : Mitusuro Sugita et al.

It is certified that error appears in the above-identified patent and that said Letters Patent is hereby corrected as shown below:

COLUMN 4:
Line 54, "29C" should read --22C--.

COLUMN 6:
Line 32, "optical" should read --an optical--.
Line 34, "optical" should read --an optical--.

COLUMN 11:
Line 57, "moves" should read --move--.

COLUMN 16:
Line 63, "cross sectional" should read --cross-sectional--.

COLUMN 18:
Line 50, "Of" should read --of--.

COLUMN 24:
Line 56, "reaches" should read --reach--.

Signed and Sealed this

Twenty-seventh Day of January, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,171,095 B2  Page 1 of 1
APPLICATION NO. : 10/545157
DATED : January 30, 2007
INVENTOR(S) : Mitsuro Sugita et al.

It is certified that error appears in the above-identified patent and that said Letters Patent is hereby corrected as shown below:

ON THE TITLE PAGE:

Item (75), Inventors, "Mitusuro Sugita" should read --Mitsuro Sugita--.

Signed and Sealed this

Seventh Day of April, 2009

JOHN DOLL
*Acting Director of the United States Patent and Trademark Office*